United States Patent
Peng et al.

(10) Patent No.: US 11,608,534 B2
(45) Date of Patent: Mar. 21, 2023

(54) METHODS OF DETECTING AN EML4-ALK FUSION TUMOR BIOMARKER

(71) Applicant: Sichuan University, Sichuan (CN)

(72) Inventors: Yong Peng, Chengdu (CN); Yuquan Wei, Chengdu (CN); Shuangyan Tan, Chengdu (CN); Ke Wu, Chengdu (CN)

(73) Assignee: Sichuan University, Sichuan (CN)

( * ) Notice: Subject to any disclaimer, the term of this patent is extended or adjusted under 35 U.S.C. 154(b) by 0 days.

(21) Appl. No.: 17/013,947

(22) Filed: Sep. 8, 2020

(65) Prior Publication Data

US 2021/0071263 A1 Mar. 11, 2021

Related U.S. Application Data

(63) Continuation-in-part of application No. PCT/CN2018/086201, filed on May 9, 2018.

(30) Foreign Application Priority Data

Mar. 8, 2018 (CN) .......................... 201810190175.1

(51) Int. Cl.
*C12Q 1/6886* (2018.01)
(52) U.S. Cl.
CPC ..... *C12Q 1/6886* (2013.01); *C12Q 2600/156* (2013.01)
(58) Field of Classification Search
None
See application file for complete search history.

(56) References Cited

U.S. PATENT DOCUMENTS

| 2014/0272956 A1 | 9/2014 | Huang et al. |
| 2016/0097103 A1* | 4/2016 | Yamagishi ........... C12Q 1/6886 435/6.11 |
| 2017/0298347 A1 | 10/2017 | Pandolfi et al. |

FOREIGN PATENT DOCUMENTS

CN 101528921 9/2009

OTHER PUBLICATIONS

Tan et al Cell Research. Apr. 8, 2018. 28: 693-695 and Supplementary information, 11 pages total (Year: 2018).*
Choi, Y.L. et al. "identification of Novel Isoforms of the EML4-ALK Transforming Gene in Non-Small Cell Lung Cancer", Cancer Research, vol. 68, No. 13, Jul. 1, 2008, pp. 4971-4976.

* cited by examiner

*Primary Examiner* — Carla J Myers
(74) *Attorney, Agent, or Firm* — Thomas | Horstemeyer, LLP

(57) ABSTRACT

Disclosed are a tumor biomarker and application thereof, and a tumor detection kit. Patients suffering from non-small cell lung cancer, containing an EML4-ALK or SLC34A2-ROS1 fusion gene, have a specific circular RNA in blood. The base sequences of the circular RNA are represented by SEQ ID NOS. 1-6. The circular RNA is associated with non-small cell lung cancer, stably and constantly exists in plasma samples, and has high specificity and effectiveness, and thus can be used as a biomarker for tumor detection. Reagents such as primers and probes for detecting the circular RNA can be used for preparing the tumor detection kit.

1 Claim, 2 Drawing Sheets

Specification includes a Sequence Listing.

SEQUENCE LISTING

```
<160> NUMBER OF SEQ ID NOS: 374

<210> SEQ ID NO 1
<211> LENGTH: 550
<212> TYPE: RNA
<213> ORGANISM: Artificial Sequence
<220> FEATURE:
<223> OTHER INFORMATION: Synthetic Sequence

<400> SEQUENCE: 1
aauucgagca ucaccuucuc cccagcccuc uucacaaccu cuccaaauac acagacaaac      60
uccagaaagc aagaaugcua cucccaccaa aagcauaaaa cgaccaucac cagcugaaaa     120
gucacauaau ucuugggaaa auucagauga uagccguaau aaauugucga aaauaccuuc     180
aacacccaaa uuaauaccaa aaguuaccaa aacugcagac aagcauaaag augucaucau     240
caaccaagug uaccgccgga agcaccagga gcugcaagcc augcagaugg agcugcagag     300
cccugaguac aagcugagca agcuccgcac cucgaccauc augaccgacu acaaccccaa     360
cuacugcuuu gcuggcaaga ccuccuccau cagugaccug aaggagggugc cgcggaaaaa     420 caucacccuc auucgggguc ugggccaugg agccuuuggg gagguguaug aaggccaggu     480
```

```
guccggaaug cccaacgacc caagccsccu gcaaguggcu gugaagacgc ugccugaagu    540
gugcucugaa                                                           550
```

<210> SEQ ID NO 2
<211> LENGTH: 548
<212> TYPE: RNA
<213> ORGANISM: Artificial Sequence
<220> FEATURE:
<223> OTHER INFORMATION: Synthetic Sequence

<400> SEQUENCE: 2

```
auucgagcau caccuucucc ccagcccucu ucacaaccuc ccaaauaca cagacaaacu     60 ccagaaagca agaaugcuac ucccaccaaa agcauaaaac gaccaucacc agcugaaaag   120
ucacauaauu cuugggaaaa ucagaugau agccguaaua aauugucgaa aauaccuuca    180
acacccaaau uaauaccaaa aguuaccaaa acugcagaca agcauaaaga ugucaucauc   240
aaccaagugu accgccggaa gcaccaggag cugcaagcca ugcagaugga gcugcagagc   300
ccugaguaca agcugagcaa gcuccgcacc ucgaccauca ugaccgacua aaccccaac    360 uacugcuuug cuggcaagac cuccuccauc agugaccuga aggaggugcc gcggaaaaac   420
aucacccuca uucggggucu ggccauggga gccuugggg aggugauga aggccaggug     480 uccggaaugc ccaacgaccc aagcccccug caaguggcug ugaagacgcu gccugaagug   540
ugcucuga                                                            548
```

<210> SEQ ID NO 3
<211> LENGTH: 583
<212> TYPE: RNA
<213> ORGANISM: Artificial Sequence
<220> FEATURE:
<223> OTHER INFORMATION: Synthetic Sequence

<400> SEQUENCE: 3

```
aauucgagca ucaccuucuc cccagcccuc uucacaaccu cccaaauac acagacaaac     60 uccagaaagc aagaaugcua cucccaccaa aagcauaaaa cgaccaucac cagcugaaaa   120
gucacauaau ucuugggaaa auucagauga uagccguaau aaauugucga aaauaccuuc   180
aacacccaaa uuaauaccaa aaguuaccaa aacugcagac aagcauaaag augucaucau   240
caaccaagca aaaaugucaa cucgcgaaaa aaacagccaa guguaccgcc ggaagcacca   300
ggagcugcaa gccaugcaga uggagcugca gagcccugag uacaagcuga gcaagcuccg   360
caccucgacc aucaugaccg acuacaaccc caacuacugc uuugcuggca agaccuccuc   420
caucagugac cugaaggagg ugccgcggaa aaacaucacc cucauucggg gucugggcca   480
uggagccuuu ggggaggugu augaaggcca ggguccgga augcccaacg acccaagccc    540
ccugcaagug gcugugaaga cgcugccuga agugugcucu gaa                    583
```

<210> SEQ ID NO 4
<211> LENGTH: 581
<212> TYPE: RNA
<213> ORGANISM: Artificial Sequence
<220> FEATURE:
<223> OTHER INFORMATION: Synthetic Sequence

<400> SEQUENCE: 4

```
auucgagcau caccuucucc ccagcccucu ucacaaccuc ccaaauaca cagacaaacu     60 ccagaaagca agaaugcuac ucccaccaaa agcauaaaac gaccaucacc agcugaaaag   120
```

| | |
|---|---:|
| ucacauaauu cuugggaaaa uucagaugau agccguaaua aauugucgaa aauaccuuca | 180 |
| acacccaaau uaauaccaaa aguuaccaaa acugcagaca agcauaaaga ugucaucauc | 240 |
| aaccaagcaa aaaugucaac ucgcgaaaaa aacagccaag uguaccgccg gaagcaccag | 300 |
| gagcugcaag ccaugcagau ggagcugcag agcccgaagu acaagcugag caagcuccgc | 360 |
| accucgacca ucaugaccga cuacaacccc aacuacugcu uugcuggcaa gaccuccucc | 420 |
| aucagugacc ugaaggaggu gccgcggaaa aacaucaccc ucauucgggg ucugggccau | 480 |
| ggagccuuug gggaggugua ugaaggccag guguccggaa ugcccaacga cccaagcccc | 540 |
| cugcaagugg cugugaagac gcugccugaa gugugcucug a | 581 |

<210> SEQ ID NO 5
<211> LENGTH: 1867
<212> TYPE: RNA
<213> ORGANISM: Artificial Sequence
<220> FEATURE:
<223> OTHER INFORMATION: Synthetic Sequence

<400> SEQUENCE: 5

| | |
|---|---:|
| accauggcuc ccuggccuga auugggagau gcccagccca accccgauaa guaccucgaa | 60 |
| ggggccgcag gucagcagcc cacugccccu gauaaaagca agagaccaa caaaacagau | 120 |
| aacacugagg caccuguaac caagauugaa cuucugccgu ccuacuccac ggcuacacug | 180 |
| auagaugagc ccacugaggu ggaugacccc uggaaccuac ccacucuuca ggacucgggg | 240 |
| aucaaguggu cagagagaga caccaaaggg aagauucucu guuucuucca agggauggg | 300 |
| agauugauuu uacuucucgg auuucucuac uuuucgugu gcucccugga uauucuuagu | 360 |
| agcgccuucc agcugguugg agcuggaguc ccaaauaaac caggcauucc caauuacua | 420 |
| gaagggagua aaaauucaau acaggggag aaagcugaag auaauggaug uagaauuaca | 480 |
| uacuauaucc uugagauaag aaagagcacu ucaauaauu uacagaacca gaauuuaagg | 540 |
| uggaagauga cauuuaaugg auccugcagu aguuuugca cauggaaguc caaaaaccug | 600 |
| aaaggaauau uucaguucag aguaguagcu gcaauaauc uagggguugg ugaauauagu | 660 |
| ggaaucagug agaauauuau auuaguugga gaugauuuuu ggauaccaga aacaaguuuc | 720 |
| auacuuacua uuauaguugg aauauuucug guuguuacaa ucccacugac cuuugucugg | 780 |
| cauagaagau uaaagaauca aaaaagugcc aaggaagggg ugacagugcu auaaacgaa | 840 |
| gacaaagagu uggcugagcu gcgaggucug gcagccggag uaggccuggc uaaugccugc | 900 |
| uaugcaauac auacucuucc aacccaagag gagauugaaa aucuuccgc cuucccucgg | 960 |
| gaaaaacuga cucugcgucu cuugcuggga aguggagccu uggagaagu guaugaagga | 1020 |
| acagcagugg acaucuuagg aguuggaagu ggagaaauca aguagcagu gaagacuuug | 1080 |
| aagaaggguu ccacagacca ggagaagauu gaauuccuga aggaggcaca ucugaugagc | 1140 |
| aaauuuaauc aucccaacau ucugaagcag cuuggaguuu gucugcugaa ugaaccccaa | 1200 |
| uacauuaucc uggaacugau ggaggagga gaccuucuua cuuauuugcg uaaagcccgg | 1260 |
| auggcaacgu uuuaugguccuuuacucacc uugguugacc uuguagaccu guguguagau | 1320 |
| auuucaaaag gcugugucua cuuggaacgg augcauuuca uucacaggga ucuggcagcu | 1380 |
| agaaauugcc uuguuccgu gaaagacuau accaguccac ggauagugaa gauuggagac | 1440 |
| uuuggacucg ccagagacau cuauaaaau gauuacuaua gaaagagagg ggaaggccug | 1500 |
| cucccagauc ggugggaugg cccagaaagu uugaaugaug gaaucuucac uacucaaucu | 1560 |
| gauguauggu cuuuuggaau ucugauuugg gagauuuuaa cucuuggca ucagccuuau | 1620 |

```
ccagcucauu ccaaccuuga uguguuaaac uaugugcaaa caggagggag acuggagcca      1680
ccaagaaauu guccugauga ucugugggaau uuaaugaccc agugcugggc ucaagaaccc     1740
```

```
ccagcucauu ccaaccuuga uguguuaaac uaugugcaaa caggagggag acuggagcca      1680
ccaagaaauu guccugauga ucugugggau uuaaugaccc agugcugggc ucaagaaccc      1740
gaccaaagac cuacuuuuca uagaauucag gaccaacuuc aguuauucag aaauuuuuuc      1800
uuaaauagca uuuauaaguc cagagaugaa gcaaacaaca guggagucau aaaugaaagc      1860
uuugaag                                                                1867
```

<210> SEQ ID NO 6
<211> LENGTH: 830
<212> TYPE: RNA
<213> ORGANISM: Artificial Sequence
<220> FEATURE:
<223> OTHER INFORMATION: Synthetic Sequence

<400> SEQUENCE: 6

```
accauggcuc ccuggccuga auugggagau gcccagccca accccgauaa guaccucgaa      60
ggggccgcag gucagcagcc cacugccccu gauaaaagca aagagaccaa caaaacagau     120
aacacugagg caccuguaac caagauugaa cuucugccgu ccuacuccac ggcuacacug     180
auagaugagc ccacugaggu ggaugacccc uggaaccuac ccacucuuca ggacucgggg     240
aucaaguggu cagagagaga caccaaaggg aagauucucu guuucuucca agggauuggg     300
agauugauuu uacuucucgg auuucucuac uuuuucgugu gcccccugga uauucuagu      360 agcgccuucc agcugguugg agaugauuuu uggauaccag aaacaaguuu cauacuuacu     420
auuauaguug gaauauuucu gguuguuaca aucccacuga ccuuugucug gcauagaaga     480
uuaaagaauc aaaaaagugc caaggaaggg gugacagugc uuauaaacga agacaaagag     540
uuggcugagc ucgaggucu ggcagccgga guaggccugg cuaaugccug cuaugcaaua     600
cauacucuuc caacccaaga ggagauugaa aaucuuccug ccuuccccg ggaaaaacug      660 acucugcguc ucuugcuggg aagugggagcc uuuggagaag uguaugaagg aacagcagug     720
gacaucuuag gaguuggaag uggagaaauc aaaguagcag ugaagacuuu gaagaagggu     780
uccacagacc aggagaagau ugaauuccug aaggaggcac aucugaugag                 830
```

<210> SEQ ID NO 7
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 7

```
gcagagccct gagtacaagc                                                   20
```

<210> SEQ ID NO 8
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 8

```
caactactgc tttgctggca                                                   20
```

<210> SEQ ID NO 9
<211> LENGTH: 20
<212> TYPE: DNA
<213> ORGANISM: Artificial Sequence
<220> FEATURE:

<223> OTHER INFORMATION: Synthetic Sequence

<400> SEQUENCE: 9
aaacatcacc ctcattcggg                                         20

<210> SEQ ID NO 10
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 10
caagaatgct actcccacca a                                       21

<210> SEQ ID NO 11
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 11
tcctccatca gtgacctgaa                                         20

<210> SEQ ID NO 12
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 12
gtgtatgaag gccaggtgtc                                         20

<210> SEQ ID NO 13
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 13
gagtacaagc tgagcaagct                                         20

<210> SEQ ID NO 14
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 14
aattcgagca tcaccttctc cccag                                   25

<210> SEQ ID NO 15
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 15
aattcgagca tcaccttctc cc                                      22

<210> SEQ ID NO 16
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 16
agccctcttc acaacctctc				20

<210> SEQ ID NO 17
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 17
cacaacctct ccaaatacac aga			23

<210> SEQ ID NO 18
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 18
aaactccaga aagcaagaat gc			22

<210> SEQ ID NO 19
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 19
gaccatcacc agctgaaaag tc			22

<210> SEQ ID NO 20
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 20
tgcagagccc tgagtacaag c				21

<210> SEQ ID NO 21
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 21
ccaactactg ctttgctggc a				21

<210> SEQ ID NO 22
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 22
ctgcaagtgg ctgtgaaga					19

<210> SEQ ID NO 23
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 23
gtgaagacgc tgcctgaa					18

<210> SEQ ID NO 24
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 24
ccatcatgac cgactacaac					20

<210> SEQ ID NO 25
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 25
tgtatgaagg ccaggtgt					18

<210> SEQ ID NO 26
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 26
ctgagtacaa gctgagcaag					20

<210> SEQ ID NO 27
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 27
catcagtgac ctgaaggag					19

<210> SEQ ID NO 28
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 28
gaagacgctg cctgaag					17

<210> SEQ ID NO 29
<211> LENGTH: 17

```
<212> TYPE: DNA
<213> ORGANISM: Artificial Sequence
<220> FEATURE:
<223> OTHER INFORMATION: Synthetic Sequence

<400> SEQUENCE: 29
tgcaagtggc tgtgaag                                                    17

<210> SEQ ID NO 30
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 30
cctgaagtgt gctctgaaa                                                  19

<210> SEQ ID NO 31
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 31
cccaactact gctttgct                                                   18

<210> SEQ ID NO 32
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 32
cgctgcctga agtgtgctct gaaaa                                           25

<210> SEQ ID NO 33
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 33
gctgcctgaa gtgtgctctg aaaat                                           25

<210> SEQ ID NO 34
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 34
ctgcctgaag tgtgctctga aaatt                                           25

<210> SEQ ID NO 35
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 35
```

```
tgcctgaagt gtgctctgaa aattc                                              25

<210> SEQ ID NO 36
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 36
gcctgaagtg tgctctgaaa attcg                                              25

<210> SEQ ID NO 37
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 37
cctgaagtgt gctctgaaaa ttcga                                              25

<210> SEQ ID NO 38
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 38
ctgaagtgtg ctctgaaaat tcgag                                              25

<210> SEQ ID NO 39
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 39
tgaagtgtgc tctgaaaatt cgagc                                              25

<210> SEQ ID NO 40
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 40
gaagtgtgct ctgaaaattc gagca                                              25

<210> SEQ ID NO 41
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 41
aagtgtgctc tgaaaattcg agcat                                              25

<210> SEQ ID NO 42
<211> LENGTH: 25
<212> TYPE: DNA
<213> ORGANISM: Artificial Sequence
```

```
<220> FEATURE:
<223> OTHER INFORMATION: Synthetic Sequence

<400> SEQUENCE: 42
agtgtgctct gaaaattcga gcatc                                             25

<210> SEQ ID NO 43
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 43
gtgtgctctg aaaattcgag catca                                             25

<210> SEQ ID NO 44
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 44
tgtgctctga aaattcgagc atcac                                             25

<210> SEQ ID NO 45
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 45
gtgctctgaa aattcgagca tcacc                                             25

<210> SEQ ID NO 46
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 46
tgctctgaaa attcgagcat cacct                                             25

<210> SEQ ID NO 47
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 47
gctctgaaaa ttcgagcatc acctt                                             25

<210> SEQ ID NO 48
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 48
ctctgaaaat tcgagcatca ccttc                                             25
```

<210> SEQ ID NO 49
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 49
tctgaaaatt cgagcatcac cttct         25

<210> SEQ ID NO 50
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 50
ctgaaaattc gagcatcacc ttctc         25

<210> SEQ ID NO 51
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 51
tgaaaattcg agcatcacct tctcc         25

<210> SEQ ID NO 52
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 52
gaaaattcga gcatcacctt ctccc         25

<210> SEQ ID NO 53
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 53
tgtgctctga aaattcgagc at         22

<210> SEQ ID NO 54
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 54
gctctgaaaa ttcgagcatc accttc         26

<210> SEQ ID NO 55
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 55
gctctgaaaa ttcgagcatc ac                                              22

<210> SEQ ID NO 56
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 56
agtgtgctct gaattcgagc                                                 20

<210> SEQ ID NO 57
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 57
gctctgaatt cgagcatcac c                                               21

<210> SEQ ID NO 58
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 58
gcctgaagtg tgctctgaat t                                               21

<210> SEQ ID NO 59
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 59
gcttggttga tgatgacatc tttatg                                          26

<210> SEQ ID NO 60
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 60
gcattcttgc tttctggagt tt                                              22

<210> SEQ ID NO 61
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 61
ttgtagtcgg tcatgatggt c                                               21

<210> SEQ ID NO 62

```
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 62
ggagaaggtg atgctcgaat t                                              21

<210> SEQ ID NO 63
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 63
gcttgctcag cttgtactca                                                20

<210> SEQ ID NO 64
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 64
ttcaggtcac tgatggagga                                                20

<210> SEQ ID NO 65
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 65
tttgcttggt tgatgatgac atc                                            23

<210> SEQ ID NO 66
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 66
ttcagagcac acttcaggca gc                                             22

<210> SEQ ID NO 67
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 67
tctgtgtatt tggagaggtt gtga                                           24

<210> SEQ ID NO 68
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 68
```
gcattcttgc tttctggagt tt                                              22

<210> SEQ ID NO 69
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 69
gcttggttga tgatgacatc tttatgc                                         27

<210> SEQ ID NO 70
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 70
tgccagcaaa gcagtagttg                                                 20

<210> SEQ ID NO 71
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 71
cacctggcct tcatacacct                                                 20

<210> SEQ ID NO 72
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 72
tcttcacagc cacttgcag                                                  19

<210> SEQ ID NO 73
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 73
ttcaggcagc gtcttcac                                                   18

<210> SEQ ID NO 74
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 74
gtcgttttat gcttttggtg ggagta                                          26

<210> SEQ ID NO 75
<211> LENGTH: 24
<212> TYPE: DNA

```
<213> ORGANISM: Artificial Sequence
<220> FEATURE:
<223> OTHER INFORMATION: Synthetic Sequence

<400> SEQUENCE: 75
gatggtcgtt ttatgctttt ggtg                                    24

<210> SEQ ID NO 76
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 76
tctggagttt gtctgtgtat tt                                      22

<210> SEQ ID NO 77
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 77
gagaaggtga tgctcgaatt t                                       21

<210> SEQ ID NO 78
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 78
tttgtctgtg tatttggaga gg                                      22

<210> SEQ ID NO 79
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 79
gagtagcatt cttgctttct g                                       21

<210> SEQ ID NO 80
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 80
tttcccaaga attatgtgac ttt                                     23

<210> SEQ ID NO 81
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 81
tatttggaga ggttgtgaag ag                                      22
```

<210> SEQ ID NO 82
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 82
ggtgggagta gcattcttg                                              19

<210> SEQ ID NO 83
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 83
tcttgctttc tggagtttgt                                             20

<210> SEQ ID NO 84
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 84
ttttcagagc acacttcagg cagcg                                       25

<210> SEQ ID NO 85
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 85
attttcagag cacacttcag gcagc                                       25

<210> SEQ ID NO 86
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 86
aattttcaga gcacacttca ggcag                                       25

<210> SEQ ID NO 87
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 87
gaattttcag agcacacttc aggca                                       25

<210> SEQ ID NO 88
<211> LENGTH: 25
<212> TYPE: DNA
<213> ORGANISM: Artificial Sequence
<220> FEATURE:

<223> OTHER INFORMATION: Synthetic Sequence

<400> SEQUENCE: 88
cgaattttca gagcacactt caggc                                          25

<210> SEQ ID NO 89
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 89
tcgaattttc agagcacact tcagg                                          25

<210> SEQ ID NO 90
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 90 ctcgaattt cagagcacac ttcag                                           25

<210> SEQ ID NO 91
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 91
gctcgaattt tcagagcaca cttca                                          25

<210> SEQ ID NO 92
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 92
tgctcgaatt ttcagagcac acttc                                          25

<210> SEQ ID NO 93
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 93
atgctcgaat tttcagagca cactt                                          25

<210> SEQ ID NO 94
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 94
gatgctcgaa ttttcagagc acact                                          25

```
<210> SEQ ID NO 95
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 95
tgatgctcga attttcagag cacac                                          25

<210> SEQ ID NO 96
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 96
gtgatgctcg aattttcaga gcaca                                          25

<210> SEQ ID NO 97
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 97
ggtgatgctc gaattttcag agcac                                          25

<210> SEQ ID NO 98
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 98
aggtgatgct cgaattttca gagca                                          25

<210> SEQ ID NO 99
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 99
aaggtgatgc tcgaattttc agagc                                          25

<210> SEQ ID NO 100
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 100
gaaggtgatg ctcgaatttt cagag                                          25

<210> SEQ ID NO 101
<211> LENGTH: 25
<212> TYPE: DNA
<213> ORGANISM: Artificial Sequence
<220> FEATURE:
<223> OTHER INFORMATION: Synthetic Sequence
```

<400> SEQUENCE: 101
agaaggtgat gctcgaatt tcaga 25

<210> SEQ ID NO 102
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 102
gagaaggtga tgctcgaatt ttcag 25

<210> SEQ ID NO 103
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 103
ggagaaggtg atgctcgaat tttca 25

<210> SEQ ID NO 104
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 104
tggggagaag gtgatgctcg aattttc 27

<210> SEQ ID NO 105
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 105
atgctcgaat tttcagagca ca 22

<210> SEQ ID NO 106
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 106
aggtgatgct cgaattttca gag 23

<210> SEQ ID NO 107
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 107
gtgatgctcg aattttcaga gc 22

<210> SEQ ID NO 108
<211> LENGTH: 20

<212> TYPE: DNA
<213> ORGANISM: Artificial Sequence
<220> FEATURE:
<223> OTHER INFORMATION: Synthetic Sequence

<400> SEQUENCE: 108
gctcgaattc agagcacact                                          20

<210> SEQ ID NO 109
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 109
ggtgatgctc gaattcagag c                                        21

<210> SEQ ID NO 110
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 110
aattcagagc acacttcagg c                                        21

<210> SEQ ID NO 111
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 111
ttccaaccca agaggagatt g                                        21

<210> SEQ ID NO 112
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 112
cagtgggaga aagctgaaga taa                                      23

<210> SEQ ID NO 113
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 113
tgtatgaagg aacagcagtg g                                        21

<210> SEQ ID NO 114
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 114
gtgaagattg gagactttgg ac                                                    22

<210> SEQ ID NO 115
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 115
catactcttc caacccaaga gg                                                    22

<210> SEQ ID NO 116
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 116
cttatccagc tcattccaac ct                                                    22

<210> SEQ ID NO 117
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 117
ctttactcac cttggttgac ct                                                    22

<210> SEQ ID NO 118
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 118
agtgtatgaa ggaacagcag tg                                                    22

<210> SEQ ID NO 119
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 119
gagatgaagc aaacaacagt gg                                                    22

<210> SEQ ID NO 120
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 120
gtatgaagga acagcagtgg a                                                     21

<210> SEQ ID NO 121
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 121
agagagagac accaaaggga                                              20

<210> SEQ ID NO 122
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 122
caatcccact gacctttgtc t                                            21

<210> SEQ ID NO 123
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 123
cacagaccag gagaagattg aa                                           22

<210> SEQ ID NO 124
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 124
gatattctta gtagcgcctt cca                                          23

<210> SEQ ID NO 125
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 125
cataaatgaa agctttgaag accat                                        25

<210> SEQ ID NO 126
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 126
tcataaatga agctttgaa gacca                                         25

<210> SEQ ID NO 127
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 127
gtcataaatg aaagctttga agacc                                        25

<210> SEQ ID NO 128
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 128
agtcataaat gaaagctttg aagac                                          25

<210> SEQ ID NO 129
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 129
ataaatgaaa gctttgaaga ccatg                                          25

<210> SEQ ID NO 130
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 130
taaatgaaag ctttgaagac catgg                                          25

<210> SEQ ID NO 131
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 131
aaatgaaagc tttgaagacc atggc                                          25

<210> SEQ ID NO 132
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 132
aatgaaagct ttgaagacca tggct                                          25

<210> SEQ ID NO 133
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 133
atgaaagctt tgaagaccat ggctc                                          25

<210> SEQ ID NO 134
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 134
tgaaagcttt gaagaccatg gctcc                                              25

<210> SEQ ID NO 135
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 135
gaaagctttg aagaccatgg ctccc                                              25

<210> SEQ ID NO 136
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 136
aaagctttga agaccatggc tccct                                              25

<210> SEQ ID NO 137
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 137
aagctttgaa gaccatggct ccctg                                              25

<210> SEQ ID NO 138
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 138
agctttgaag accatggctc cctgg                                              25

<210> SEQ ID NO 139
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 139
gctttgaaga ccatggctcc ctggc                                              25

<210> SEQ ID NO 140
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 140
ctttgaagac catggctccc tggcc                                              25

<210> SEQ ID NO 141

<211> LENGTH: 25
<212> TYPE: DNA
<213> ORGANISM: Artificial Sequence
<220> FEATURE:
<223> OTHER INFORMATION: Synthetic Sequence

<400> SEQUENCE: 141
tttgaagacc atggctccct ggcct                                    25

<210> SEQ ID NO 142
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 142
ttgaagacca tggctccctg gcctg                                    25

<210> SEQ ID NO 143
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 143
tgaagaccat ggctccctgg cctga                                    25

<210> SEQ ID NO 144
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 144
gaagaccatg gctccctggc ctgaa                                    25

<210> SEQ ID NO 145
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 145
aagaccatgg ctccctggcc tgaat                                    25

<210> SEQ ID NO 146
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 146
agaccatggc tccctggcct gaatt                                    25

<210> SEQ ID NO 147
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 147

-continued ctgaaggagg cacatctgat gagac 25

<210> SEQ ID NO 148
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 148
tgaaggaggc acatctgatg agacc 25

<210> SEQ ID NO 149
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 149
gaaggaggca catctgatga gacca 25

<210> SEQ ID NO 150
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 150
aaggaggcac atctgatgag accat 25

<210> SEQ ID NO 151
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 151
aggaggcaca tctgatgaga ccatg 25

<210> SEQ ID NO 152
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 152
ggaggcacat ctgatgagac catgg 25

<210> SEQ ID NO 153
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 153
gaggcacatc tgatgagacc atggc 25

<210> SEQ ID NO 154
<211> LENGTH: 25
<212> TYPE: DNA

<213> ORGANISM: Artificial Sequence
<220> FEATURE:
<223> OTHER INFORMATION: Synthetic Sequence

<400> SEQUENCE: 154
aggcacatct gatgagacca tggct					25

<210> SEQ ID NO 155
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 155
ggcacatctg atgagaccat ggctc					25

<210> SEQ ID NO 156
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 156
gcacatctga tgagaccatg gctcc					25

<210> SEQ ID NO 157
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 157
cacatctgat gagaccatgg ctccc					25

<210> SEQ ID NO 158
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 158
acatctgatg agaccatggc tccct					25

<210> SEQ ID NO 159
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 159
catctgatga gaccatggct ccctg					25

<210> SEQ ID NO 160
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 160
atctgatgag accatggctc cctgg					25

<210> SEQ ID NO 161
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 161
tctgatgaga ccatggctcc ctggc                                        25

<210> SEQ ID NO 162
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 162
ctgatgagac catggctccc tggcc                                        25

<210> SEQ ID NO 163
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 163
tgatgagacc atggctccct ggcct                                        25

<210> SEQ ID NO 164
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 164
gatgagacca tggctccctg gcctg                                        25

<210> SEQ ID NO 165
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 165
atgagaccat ggctccctgg cctga                                        25

<210> SEQ ID NO 166
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 166
tgagaccatg gctccctggc ctgaa                                        25

<210> SEQ ID NO 167
<211> LENGTH: 25
<212> TYPE: DNA
<213> ORGANISM: Artificial Sequence
<220> FEATURE:

<223> OTHER INFORMATION: Synthetic Sequence

<400> SEQUENCE: 167
gagaccatgg ctccctggcc tgaat                                  25

<210> SEQ ID NO 168
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 168
aagaccatgg ctccctggcc tgaatt                                 26

<210> SEQ ID NO 169
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 169
gatggatgga atcttcacta ctc                                    23

<210> SEQ ID NO 170
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 170
ctcaagaacc cgaccaaag                                         19

<210> SEQ ID NO 171
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 171
cttaaatagc atttataagt ccagagatg                              29

<210> SEQ ID NO 172
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 172
cagccttatc cagctcattc                                        20

<210> SEQ ID NO 173
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 173
tgtggaattt aatgacccag t                                      21

```
<210> SEQ ID NO 174
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 174
gaccaacttc agttattcag aaat                                           24

<210> SEQ ID NO 175
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 175
tgaagcaaac aacagtggag                                                20

<210> SEQ ID NO 176
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 176
ttcatagaat tcaggaccaa ct                                             22

<210> SEQ ID NO 177
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 177
agtgctgggc tcaagaa                                                   17

<210> SEQ ID NO 178
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 178
accaagaaat tgtcctgatg at                                             22

<210> SEQ ID NO 179
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 179
tgcaaacagg agggaga                                                   17

<210> SEQ ID NO 180
<211> LENGTH: 18
<212> TYPE: DNA
<213> ORGANISM: Artificial Sequence
<220> FEATURE:
<223> OTHER INFORMATION: Synthetic Sequence
```

<400> SEQUENCE: 180
ctggagccac caagaaat                                                 18

<210> SEQ ID NO 181
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 181
attcaggacc aacttcagtt at                                            22

<210> SEQ ID NO 182
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 182
gtcctgatga tctgtggaat tta                                           23

<210> SEQ ID NO 183
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 183
actcaatctg atgtatggtc ttt                                           23

<210> SEQ ID NO 184
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 184
caaacaacag tggagtcata aat                                           23

<210> SEQ ID NO 185
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 185
gtccagagat gaagcaaaca                                               20

<210> SEQ ID NO 186
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 186
cagctagaaa ttgccttgtt tc                                            22

<210> SEQ ID NO 187
<211> LENGTH: 20

<212> TYPE: DNA
<213> ORGANISM: Artificial Sequence
<220> FEATURE:
<223> OTHER INFORMATION: Synthetic Sequence

<400> SEQUENCE: 187
ggagtttgtc tgctgaatga                                          20

<210> SEQ ID NO 188
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 188
ccttgtagac ctgtgtgtag a                                        21

<210> SEQ ID NO 189
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 189
gtgtctactt ggaacggatg                                          20

<210> SEQ ID NO 190
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 190
cagggatctg gcagcta                                             17

<210> SEQ ID NO 191
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 191
ccttggttga ccttgtagac                                          20

<210> SEQ ID NO 192
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 192
aggctgtgtc tacttgga                                            18

<210> SEQ ID NO 193
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 193

```
gcatttcatt cacagggatc t                                              21

<210> SEQ ID NO 194
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 194
gaacggatgc atttcattca c                                              21

<210> SEQ ID NO 195
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 195
ggatctggca gctagaaatt g                                              21

<210> SEQ ID NO 196
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 196
gtgaaagact ataccagtcc ac                                             22

<210> SEQ ID NO 197
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 197
gggaggagac cttcttactt                                                20

<210> SEQ ID NO 198
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 198
tgtttccgtg aaagactata cc                                             22

<210> SEQ ID NO 199
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 199
ggagaagtgt atgaaggaac ag                                             22

<210> SEQ ID NO 200
<211> LENGTH: 21
<212> TYPE: DNA
<213> ORGANISM: Artificial Sequence
```

```
<220> FEATURE:
<223> OTHER INFORMATION: Synthetic Sequence

<400> SEQUENCE: 200
ttacaatccc actgaccttt g                                               21

<210> SEQ ID NO 201
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 201
ggagttggaa gtggagaaat c                                               21

<210> SEQ ID NO 202
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 202
aaagtgccaa ggaaggg                                                    17

<210> SEQ ID NO 203
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 203
gactttgaag aagggttcca                                                 20

<210> SEQ ID NO 204
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 204
tggaagtgga gaaatcaaag tag                                             23

<210> SEQ ID NO 205
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 205
tagcagtgaa gactttgaag aa                                              22

<210> SEQ ID NO 206
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 206
gaaatcaaag tagcagtgaa gac                                             23
```

```
<210> SEQ ID NO 207
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 207
gagcctttgg agaagtgtat g                                              21

<210> SEQ ID NO 208
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 208
agtggagcct ttggagaa                                                  18

<210> SEQ ID NO 209
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 209
cagtggacat cttaggagtt g                                              21

<210> SEQ ID NO 210
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 210
gaacagcagt ggacatctt                                                 19

<210> SEQ ID NO 211
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 211
catcttagga gttggaagtg g                                              21

<210> SEQ ID NO 212
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 212
ctggctaatg cctgctatg                                                 19

<210> SEQ ID NO 213
<211> LENGTH: 21
<212> TYPE: DNA
<213> ORGANISM: Artificial Sequence
<220> FEATURE:
<223> OTHER INFORMATION: Synthetic Sequence
```

```
<400> SEQUENCE: 213
gtgggagaaa gctgaagata a                                      21

<210> SEQ ID NO 214
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 214
ggatcctgca gtagtgtttg                                        20

<210> SEQ ID NO 215
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 215
accaggcatt cccaaattac                                        20

<210> SEQ ID NO 216
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 216
aagctgaaga taatggatgt agaa                                   24

<210> SEQ ID NO 217
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 217
ttcagagtag tagctgcaaa taa                                    23

<210> SEQ ID NO 218
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 218
agtagctgca aataatctag gg                                     22

<210> SEQ ID NO 219
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 219
aaccagaatt taaggtggaa ga                                     22

<210> SEQ ID NO 220
```

```
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 220
gggtttggtg aatatagtgg aa                                              22

<210> SEQ ID NO 221
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 221
cccaaattac tagaagggag taaa                                            24

<210> SEQ ID NO 222
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 222
ttcaatacag tgggagaaag c                                               21

<210> SEQ ID NO 223
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 223
gtgaatatag tggaatcagt gaga                                            24

<210> SEQ ID NO 224
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 224
gcaaataatc tagggtttgg tg                                              22

<210> SEQ ID NO 225
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 225
tcccaaataa accaggcatt c                                               21

<210> SEQ ID NO 226
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 226
```

-continued cagtagtgtt tgcacatgga                     20

<210> SEQ ID NO 227
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 227
gagataagaa agagcacttc aaataa               26

<210> SEQ ID NO 228
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 228
ggataccaga aacaagtttc atac                 24

<210> SEQ ID NO 229
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 229
gaaaggaata tttcagttca gagtag               26

<210> SEQ ID NO 230
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 230
gaatttaagg tggaagatga cattta               26

<210> SEQ ID NO 231
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 231
gcattcccaa attactagaa gg                   22

<210> SEQ ID NO 232
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 232
tccttgagat aagaaagagc ac                   22

<210> SEQ ID NO 233
<211> LENGTH: 18
<212> TYPE: DNA

```
<213> ORGANISM: Artificial Sequence
<220> FEATURE:
<223> OTHER INFORMATION: Synthetic Sequence

<400> SEQUENCE: 233
tgcacatgga agtccaaa                                                    18

<210> SEQ ID NO 234
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 234
atagttggaa tatttctggt tgt                                              23

<210> SEQ ID NO 235
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 235
gcacttcaaa taatttacag aacca                                            25

<210> SEQ ID NO 236
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 236
agatgacatt taatggatcc tg                                               22

<210> SEQ ID NO 237
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 237
agtcataaat gaaagctttg aagaccatg                                        29

<210> SEQ ID NO 238
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 238
ttgaagacca tggctccctg                                                  20

<210> SEQ ID NO 239
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 239
aaagctttga agaccatggc tc                                               22
```

<210> SEQ ID NO 240
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 240
cacatctgat gagaccatgg ctc                                              23

<210> SEQ ID NO 241
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 241
ctgatgagac catggctcc                                                   19

<210> SEQ ID NO 242
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 242
atgagaccat ggctccctg                                                   19

<210> SEQ ID NO 243
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 243
tcctgaagag tgggtaggtt                                                  20

<210> SEQ ID NO 244
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 244
tttatttggg actccagctc c                                                21

<210> SEQ ID NO 245
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 245
tcatacactt ctccaaaggc tc                                               22

<210> SEQ ID NO 246
<211> LENGTH: 21
<212> TYPE: DNA
<213> ORGANISM: Artificial Sequence
<220> FEATURE:

<223> OTHER INFORMATION: Synthetic Sequence

<400> SEQUENCE: 246
caatctcctc ttgggttgga a                                                    21

<210> SEQ ID NO 247
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 247
ctaagaatat ccagggagca cac                                                  23

<210> SEQ ID NO 248
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 248
ggataaggct gatgaccaag ag                                                   22

<210> SEQ ID NO 249
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 249
tcaatctcct cttgggttgg aa                                                   22

<210> SEQ ID NO 250
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 250
tatcagtgta gccgtggagt a                                                    21

<210> SEQ ID NO 251
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 251
aatcatctcc aaccagctgg                                                      20

<210> SEQ ID NO 252
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 252
taagatgtcc actgctgttc c                                                    21

```
<210> SEQ ID NO 253
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 253
aatcttccct ttggtgtctc tc                                              22

<210> SEQ ID NO 254
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 254
atggtcttca aagctttcat ttatg                                           25

<210> SEQ ID NO 255
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 255
tggtcttcaa agctttcatt tatga                                           25

<210> SEQ ID NO 256
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 256
ggtcttcaaa gctttcattt atgac                                           25

<210> SEQ ID NO 257
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 257
gtcttcaaag ctttcattta tgact                                           25

<210> SEQ ID NO 258
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 258
catggtcttc aaagctttca tttat                                           25

<210> SEQ ID NO 259
<211> LENGTH: 25
<212> TYPE: DNA
<213> ORGANISM: Artificial Sequence
<220> FEATURE:
<223> OTHER INFORMATION: Synthetic Sequence
```

<400> SEQUENCE: 259
ccatggtctt caaagctttc attta                                    25

<210> SEQ ID NO 260
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 260
gccatggtct tcaaagcttt cattt                                    25

<210> SEQ ID NO 261
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 261
agccatggtc ttcaaagctt tcatt                                    25

<210> SEQ ID NO 262
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 262
gagccatggt cttcaaagct ttcat                                    25

<210> SEQ ID NO 263
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 263
ggagccatgg tcttcaaagc tttca                                    25

<210> SEQ ID NO 264
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 264
gggagccatg gtcttcaaag ctttc                                    25

<210> SEQ ID NO 265
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 265
agggagccat ggtcttcaaa gcttt                                    25

<210> SEQ ID NO 266
<211> LENGTH: 25

```
<212> TYPE: DNA
<213> ORGANISM: Artificial Sequence
<220> FEATURE:
<223> OTHER INFORMATION: Synthetic Sequence

<400> SEQUENCE: 266
cagggagcca tggtcttcaa agctt                                               25

<210> SEQ ID NO 267
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 267
ccagggagcc atggtcttca aagct                                               25

<210> SEQ ID NO 268
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 268
gccagggagc catggtcttc aaagc                                               25

<210> SEQ ID NO 269
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 269
ggccagggag ccatggtctt caaag                                               25

<210> SEQ ID NO 270
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 270
aggccaggga gccatggtct tcaaa                                               25

<210> SEQ ID NO 271
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 271
caggccaggg agccatggtc ttcaa                                               25

<210> SEQ ID NO 272
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 272
```
tcaggccagg gagccatggt cttca                    25

<210> SEQ ID NO 273
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 273
attcaggcca gggagccatg gtctt                    25

<210> SEQ ID NO 274
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 274
ttcaggccag ggagccatgg tcttc                    25

<210> SEQ ID NO 275
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 275
aattcaggcc agggagccat ggtct                    25

<210> SEQ ID NO 276
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 276
gtctcatcag atgtgcctcc ttcag                    25

<210> SEQ ID NO 277
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 277
ggtctcatca gatgtgcctc cttca                    25

<210> SEQ ID NO 278
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 278
tggtctcatc agatgtgcct ccttc                    25

<210> SEQ ID NO 279
<211> LENGTH: 25
<212> TYPE: DNA
<213> ORGANISM: Artificial Sequence

```
<220> FEATURE:
<223> OTHER INFORMATION: Synthetic Sequence

<400> SEQUENCE: 279
atggtctcat cagatgtgcc tcctt                                              25

<210> SEQ ID NO 280
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 280
catggtctca tcagatgtgc ctcct                                              25

<210> SEQ ID NO 281
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 281
ccatggtctc atcagatgtg cctcc                                              25

<210> SEQ ID NO 282
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 282
gccatggtct catcagatgt gcctc                                              25

<210> SEQ ID NO 283
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 283
agccatggtc tcatcagatg tgcct                                              25

<210> SEQ ID NO 284
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 284
gagccatggt ctcatcagat gtgcc                                              25

<210> SEQ ID NO 285
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 285
ggagccatgg tctcatcaga tgtgc                                              25
```

<210> SEQ ID NO 286
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 286
gggagccatg gtctcatcag atgtg                                    25

<210> SEQ ID NO 287
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 287
agggagccat ggtctcatca gatgt                                    25

<210> SEQ ID NO 288
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 288
cagggagcca tggtctcatc agatg                                    25

<210> SEQ ID NO 289
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 289
ccagggagcc atggtctcat cagat                                    25

<210> SEQ ID NO 290
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 290
gccagggagc catggtctca tcaga                                    25

<210> SEQ ID NO 291
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 291
ggccagggag ccatggtctc atcag                                    25

<210> SEQ ID NO 292
<211> LENGTH: 25
<212> TYPE: DNA
<213> ORGANISM: Artificial Sequence
<220> FEATURE:
<223> OTHER INFORMATION: Synthetic Sequence

```
<400> SEQUENCE: 292
aggccaggga gccatggtct catca                                              25

<210> SEQ ID NO 293
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 293
caggccaggg agccatggtc tcatc                                              25

<210> SEQ ID NO 294
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 294
tcaggccagg gagccatggt ctcat                                              25

<210> SEQ ID NO 295
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 295
ttcaggccag ggagccatgg tctca                                              25

<210> SEQ ID NO 296
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 296
attcaggcca gggagccatg gtctc                                              25

<210> SEQ ID NO 297
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 297
caattcaggc cagggagcca tggtct                                             26

<210> SEQ ID NO 298
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 298
cctcagtggg ctcatctat                                                     19

<210> SEQ ID NO 299
```

```
<210> SEQ ID NO 299
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 299
tcccttggaa gaaacagaga at                                          22

<210> SEQ ID NO 300
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 300
cccaattcag gccaggga                                               18

<210> SEQ ID NO 301
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 301
caggtgcctc agtgttatct                                             20

<210> SEQ ID NO 302
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 302
tggtcttcaa agctttcatt tat                                         23

<210> SEQ ID NO 303
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 303
ggggtcatcc acctcagt                                               18

<210> SEQ ID NO 304
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 304
cccttcgagg tacttatcgg                                             20

<210> SEQ ID NO 305
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 305
```

```
gctttcattt atgactccac tg                                              22

<210> SEQ ID NO 306
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 306
tcttggttac aggtgcctca                                                 20

<210> SEQ ID NO 307
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 307
aagagtgggt aggttccagg                                                 20

<210> SEQ ID NO 308
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 308
tgggctcatc tatcagtgta                                                 20

<210> SEQ ID NO 309
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 309
ggagccatgg tcttcaaa                                                   18

<210> SEQ ID NO 310
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 310
ctgggcatct cccaattc                                                   18

<210> SEQ ID NO 311
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 311
acagagaatc ttccctttgg tg                                              22

<210> SEQ ID NO 312
<211> LENGTH: 19
<212> TYPE: DNA
```

```
<213> ORGANISM: Artificial Sequence
<220> FEATURE:
<223> OTHER INFORMATION: Synthetic Sequence

<400> SEQUENCE: 312
gagtaggacg gcagaagtt                                                  19

<210> SEQ ID NO 313
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 313
cagtgtagcc gtggagtag                                                  19

<210> SEQ ID NO 314
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 314
ggaaggcgct actaagaata tc                                              22

<210> SEQ ID NO 315
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 315
acctcagtgg gctcatctat                                                 20

<210> SEQ ID NO 316
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 316
cttccctttg gtgtctctct                                                 20

<210> SEQ ID NO 317
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 317
tcccaatccc ttggaagaaa c                                               21

<210> SEQ ID NO 318
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 318
tgtctctctc tgaccacttg a                                               21
```

-continued

```
<210> SEQ ID NO 319
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 319
ccccttcgag gtacttatcg g                                              21

<210> SEQ ID NO 320
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 320
atcccttgga agaaacagag aat                                            23

<210> SEQ ID NO 321
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 321
aggggtcatc cacctcagt                                                 19

<210> SEQ ID NO 322
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 322
atcttggtta caggtgcctc a                                              21

<210> SEQ ID NO 323
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 323
aagagtgggt aggttccagg g                                              21

<210> SEQ ID NO 324
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 324
gtgggctcat ctatcagtgt a                                              21

<210> SEQ ID NO 325
<211> LENGTH: 19
<212> TYPE: DNA
<213> ORGANISM: Artificial Sequence
<220> FEATURE:
```

<223> OTHER INFORMATION: Synthetic Sequence

<400> SEQUENCE: 325
ctgggcatct cccaattca                                        19

<210> SEQ ID NO 326
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 326
acaggtgcct cagtgttatc t                                     21

<210> SEQ ID NO 327
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 327
ggagtaggac ggcagaagtt                                       20

<210> SEQ ID NO 328
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 328
ccaatccctt ggaagaaaca                                       20

<210> SEQ ID NO 329
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 329
gtgtctctct ctgaccactt ga                                    22

<210> SEQ ID NO 330
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 330
cctcagtggg ctcatctatc a                                     21

<210> SEQ ID NO 331
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 331
ggctcatcta tcagtgtagc c                                     21

```
<210> SEQ ID NO 332
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 332
ttggttacag gtgcctca                                                   18

<210> SEQ ID NO 333
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 333
aagagtgggt aggttccagg gg                                              22

<210> SEQ ID NO 334
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 334
ggcagaagtt caatcttggt tac                                             23

<210> SEQ ID NO 335
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 335
ctgggcatct cccaattcag                                                 20

<210> SEQ ID NO 336
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 336
tacaggtgcc tcagtgttat ct                                              22

<210> SEQ ID NO 337
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 337
aacagagaat cttccctttg gtg                                             23

<210> SEQ ID NO 338
<211> LENGTH: 21
<212> TYPE: DNA
<213> ORGANISM: Artificial Sequence
<220> FEATURE:
<223> OTHER INFORMATION: Synthetic Sequence
```

<400> SEQUENCE: 338
tggagtagga cggcagaagt t                                              21

<210> SEQ ID NO 339
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 339
gagtcctgaa gagtgggtag                                                20

<210> SEQ ID NO 340
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 340
tcagtgtagc cgtggagtag                                                20

<210> SEQ ID NO 341
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 341
tggaaggcgc tactaagaat atc                                            23

<210> SEQ ID NO 342
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 342
tggaaggcgc tactaaga                                                  18

<210> SEQ ID NO 343
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 343
aggtgcctca gtgttatct                                                 19

<210> SEQ ID NO 344
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 344
ctcagtgggc tcatctatca                                                20

<210> SEQ ID NO 345
<211> LENGTH: 20

<212> TYPE: DNA
<213> ORGANISM: Artificial Sequence
<220> FEATURE:
<223> OTHER INFORMATION: Synthetic Sequence

<400> SEQUENCE: 345
gtctctctct gaccacttga                                               20

<210> SEQ ID NO 346
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 346
agtgtagccg tggagtag                                                 18

<210> SEQ ID NO 347
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 347
agtcctgaag agtgggtag                                                19

<210> SEQ ID NO 348
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 348
cccttggaag aaacagagaa t                                             21

<210> SEQ ID NO 349
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 349
ttccctttgg tgtctctct                                                19

<210> SEQ ID NO 350
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 350
agtaggacgg cagaagtt                                                 18

<210> SEQ ID NO 351
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 351

-continued cccaatccct tggaagaaac                                              20

<210> SEQ ID NO 352
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 352
aagtagagaa atccgagaag taaa                                         24

<210> SEQ ID NO 353
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 353
gcagaagttc aatcttggtt ac                                           22

<210> SEQ ID NO 354
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 354
tgggcatctc ccaattca                                                18

<210> SEQ ID NO 355
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 355
cagagaatct tccctttggt g                                            21

<210> SEQ ID NO 356
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 356
ggcgctacta agaatatcca g                                            21

<210> SEQ ID NO 357
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 357
aaatcaatct cccaatccct t                                            21

<210> SEQ ID NO 358
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 358
agaatatcca gggagcaca                                                      19

<210> SEQ ID NO 359
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 359
aagagtgggt aggttccag                                                      19

<210> SEQ ID NO 360
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 360
gctcatctat cagtgtagcc                                                     20

<210> SEQ ID NO 361
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 361
tggttacagg tgcctca                                                        17

<210> SEQ ID NO 362
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 362
gggtcatcca cctcagt                                                        17

<210> SEQ ID NO 363
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 363
cccttcgagg tacttatcg                                                      19

<210> SEQ ID NO 364
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 364
ccaattcagg ccaggga                                                        17

<210> SEQ ID NO 365
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 365
tttgttggtc tctttgcttt                                               20

<210> SEQ ID NO 366
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 366
catggtcttc aaagctttca tttatgact                                     29

<210> SEQ ID NO 367
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 367
cagggagcca tggtcttcaa                                               20

<210> SEQ ID NO 368
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 368
gagccatggt cttcaaagct tt                                            22

<210> SEQ ID NO 369
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 369
gagccatggt ctcatcagat gtg                                           23

<210> SEQ ID NO 370
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 370
ggagccatgg tctcatcag                                                19

<210> SEQ ID NO 371
<211> LENGTH: 19
<212> TYPE: DNA
<213> ORGANISM: Artificial Sequence
<220> FEATURE:
<223> OTHER INFORMATION: Synthetic Sequence

```
<400> SEQUENCE: 371
cagggagcca tggtctcat                                                19

<210> SEQ ID NO 372
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 372
gctctgaaaa ttcgag                                                   16

<210> SEQ ID NO 373
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 373
aaagctttga agaccatggc tccc                                          24

<210> SEQ ID NO 374
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 374
acatctgatg agaccatggc tccc                                          24
```

METHODS OF DETECTING AN EML4-ALK FUSION TUMOR BIOMARKER

CROSS-REFERENCE TO RELATED APPLICATIONS

The present disclosure is a continuation-in-part application of the international application number PCT/CN2018/086201 filed on May 9, 2018 and claiming priority of CN application number 201810190175.1 filed on Mar. 8, 2018, the contents of all of which are incorporated herein by reference.

REFERENCE TO A SEQUENCE LISTING

This application contains a sequence listing as an ASCII text file identified by the file name "Revised Sequence Listing P1100834.txt" created on Apr. 19, 2022 and having a size of 76,058 bytes which is incorporated herein by reference

TECHNICAL FIELD

The present disclosure relates to the field of biotechnologies and medicine, in particular to a tumor biomarker, application (use) and a tumor detection kit.

BACKGROUND ART

Lung cancer is currently the tumor with the highest mortality and incidence in the world, and over 85% is non-small cell lung cancer (NSCLC). Due to limited diagnostic methods, Most NSCLC patients are diagnosed at an advanced stage when first diagnosed, thereby missing the opportunity for surgery. Traditional chemotherapy has limited effect in the treatment of NSCLC, and the median survival is often less than one year after diagnosis. In recent years, researches on the molecular mechanism of lung cancer have made great progress, which can achieve satisfactory therapeutic effect on NSCLC by determining the molecular type of the lung cancer, and selecting a targeted drug adapted to target. Gene fusion is a chimeric gene consisting of two or more genes whose coding regions are connected end to end and placed under the control of the same set of regulatory sequences (including promoters, an enhancers, ribosome binding sequences, terminator, etc.). The echinoderm microtubule associated protein like 4 (EML4) and anaplastic lymphoma kinase (ALK) fusion gene has been found in NSCLC. The EML4-ALK fusion gene is a cancer-promoting gene mutation, accounting for 4-5% of the incidence of NSCLC. EML4-ALK causes abnormal expression of tyrosine kinase, causing malignant transformation of cells. In clinical NSCLC patients with EML4-ALK fusion gene positive, the use of crizotinib can significantly prolong the overall survival of these patients. The incidence of SL34A2-ROS1 fusion gene in NSCLC is approximately 1.0%-3.4%, and the incidence in EGFR/KRAS/ALK—negative individuals is 5.7%, the main pathological type is adenocarcinoma. The SL34A2-ROS1 genes lose extracellular domain, when fusion occurs, and retain transmembrane and intracellular tyrosine kinase domain, with main fusion sites in exons 32, 34, 35, and 36 of ROS1 gene. ROS1 receptor tyrosine kinase is involved in the activation of multiple downstream signal transduction pathways, including RAS-MAPK/ERK, PI3K/AKT/mTOR, JAK/STAT3, PLC/IP3 and SHP2/VAV3 pathways, thereby regulating of tumor cell growth, proliferation, cell cycle, differentiation, metastasis and migration. The ROS1 and ALK gene have 49% homology in the sequences of tyrosine kinase domain, the ATP binding site in the kinase catalytic domain has a homology of 77%, so the ALK inhibitor crizotinib has shown significant efficacy in the treatment of ROS1 fusion gene positive NSCLC. The ROS1 fusion gene provides a new treatment options for individualized treatment of lung cancer, and it is of important significance for clinical practice to determine the positive rate of the ROS1 fusion gene in lung adenocarcinoma, understand clinical pathological characteristics of positive patients and deduce the vulnerable population.

Researches have find that fusion mechanism of EML4 and ALK is that paracentric inversion on the short arm of chromosome 2, which in turn generates a fusion gene, and usually the fusion between different exons of EML4 and exon 20 of ALK generates different fusion types. Types of EML4-ALK fusion gene include E13-A20, E6a/b-A20, E20-A20, E15-A20, E14-A20, E18-A20, E2-A20, E17-A20, etc. The common types are E13-A20 (V1) and E6alb-A20 (V3a/b). The EML4 and ALK gene fusion generates oncogenic activity by activating of ALK kinase. Currently, crizotinib, a targeted drug for fusion protein EML4-ALK, has been approved by the US Food and Drug Administration, and is listed in the guideline as first-line drug for patients with positive ALK rearrangement (NCCN version 3. 2017). Meanwhile, the second-generation ALK inhibitors ceritinib and alectinib have been launched, and approved by the US Food and Drug Administration for use in crizotinib-resistant ALK positive NSCLC. With the successful development and clinical use of drugs targeting ALKand ROS1 positivity, the following question is what technical approach to screening patients with explicit gene fusion mutations? At present, the methods conventionally used are as follows: 1. Fluorescence in situ hybridization (FISH) technology, which is gold standard for detecting fusion genes at present, but the inability to distinguish between different variants and the high cost, which limits the wide application of this method. 2. Reverse transcription PCR (RT-PCR), which has the characteristics of rapid diagnosis and high sensitivity, but it requires high quality of RNA in samples, and there are blind spot for the detection of variation types, which makes clinical popularization difficult; 3. Immunohistochemistry (IHC), which determines the presence or absence of fusion by detecting expression of a specific antigen, characterized by low cost and relative simplicity, but relatively low detection sensitivity, and it is also incapability of distinguishing variation types of fusion. In addition, all of the above methods require a large amount of high-quality clinical tissue samples, which are often difficult to obtain. Therefore, there is an urgent clinical need to establish a simple and convenient method for the detection of EML4-ALK and SLC34A2-ROS1 fusion genes with sensitivity and specificity.

SUMMARY

Circular RNA (circRNA), a kind of endogenous non-coding RNA, possesses the potential of disease marker, which has the characteristics of conservativeness, richness and tissue specificity. Studies have find that the circRNA has correlation with tumors, and is enriched in blood exosomes. However, the traditional clinical tumor biomarkers, such as CEA, which is common in gastrointestinal tumors, have the problem of poor tissue specificity; tissue biopsy and immunohistochemistry involve invasive procedures, and often require multiple times of puncturing so as to obtain a definite pathological result. Therefore, circRNA can act as a novel biomarker for tumors.

The object of the present disclosure includes, but is not limited to, providing a tumor biomarker, which is circRNA having a base sequence as represented by any one of SEQ ID NOS. 1-6.

Another object of the present disclosure includes, but is not limited to, providing use of the above biomarkers.

Another object of the present disclosure includes, but is not limited to, providing a tumor detection kit.

The present disclosure is realized as follows:

A tumor biomarker, which is a circRNA selected from the group consisting of SEQ ID NOS. 1-6.

It should be noted that sequences represented by SEQ ID NOS. 1-6 are linear forms of the circRNA.

Use of a primers or a probes for detecting the above biomarkers in the preparation of tumor detection kits.

Further, in some embodiments of the present disclose, the tumor is lung cancer.

Further, in some embodiments of the present disclose, the lung cancer is NSCLC.

Further, in some embodiments of the present disclosure, the NSCLC is associated with the fusion of echinoderm microtubule associated protein-Like 4 (EML4) gene and Anaplastic lymphoma kinase (ALK) gene (EML4-ALK), or the NSCLC is associated with the fusion of solute carried family 34 member 2 gene and ROS proto-oncogene 1, receptor tyrosine kinase gene (SLC34A2-ROS1).

In the above, SEQ ID NOS. 1-4 are markers for fusion of two genes, EML4 and ALK, by fusion types V3a and V3b, and SEQ ID NOS. 5-6 are markers for the fusion of two genes of SLC34A2 and ROS1.

Further, in some embodiments of the present disclose, the primer is selected from the group consisting of SEQ ID NOS. 7-371.

Further, in some embodiments of the present disclosure, the primer includes: any one selected from the group consisting of SEQ ID NOS. 7-58 and any one selected from the group consisting of SEQ ID NOS. 59-110; alternatively, the primer includes: any one selected from the group consisting of SEQ ID NOS.111-242 and any one selected from the group consisting of SEQ ID NOS. 243-371.

It should be noted that, the person skilled in the art, on the premise that the circRNA shown in SEQ ID NOS. 1-6 is disclosed in this disclosure, it could quite easily select any one of the primers from SEQ ID NOS. 7-58 and any one of the primers from SEQ ID NOS. 59-110, and combine them for detecting the circRNA represented by SEQ ID NO. 1, SEQ ID NO. 3 or SEQ ID NO. 2, SEQ ID NO. 4; accordingly, it would be easy for those skilled in the art to select any one of the primers from SEQ ID NOS. 111-242 and any one of the primers from SEQ ID NOS. 243-371, and combine them for detecting the circRNA as represented by SEQ ID NO. 5 or 6.

Further, in some embodiments of the present disclosure, the primer includes a combination of SEQ ID NO. 7 and SEQ ID NO. 59 or the primer includes a combination of SEQ ID NO. 8 and SEQ ID NO. 60.

Further, in some embodiments of the present disclosure, the primer includes a combination of SEQ ID NO. 113 and SEQ ID NO. 243, or the primer includes a combination of SEQ ID NO. 114 and SEQ ID NO. 243.

Further, in some embodiments of the present disclosure, the primer includes a combination of SEQ ID NO. 111 and SEQ ID NO. 243, or the primer includes a combination of SEQ ID NO. 112 and SEQ ID NO. 243.

A tumor detection kit, which includes a reagent for detecting a circRNA in a sample, wherein the circRNA has a base sequence as represented by any one of SEQ ID NOS. 1-6.

Further, in some embodiments of the present disclosure, the reagent is a primer, and the primer comprises any one selected from SEQ ID NOS. 7-58 and any one selected from SEQ ID NOS. 59-110; alternatively, the primer comprises any one selected from SEQ ID NOS. 111-242 and any one selected from SEQ ID NOS. 243-371.

In the above, a combination of any one of SEQ ID NOS. 7-58 and any one of SEQ ID NOS. 59-110 can detect the circRNA represented by SEQ ID NOS. 1-4, and a combination of any one of SEQ ID NOS. 111-242 and any one of SEQ ID NOS. 243-371 can detect the rcRNA represented by SEQ ID NOS. 5-6.

Further, in some embodiments of the present disclosure, the above reagent is a probe.

Further, in some embodiments of the present disclosure, the above mentioned sample is blood or a blood product prepared therefrom, such as plasma.

Further, in some embodiments of the present disclose, the tumor is lung cancer.

Further, in some embodiments of the present disclose, the lung cancer is non-small cell lung cancer.

Further, in some embodiments of the present disclosure, the non-small cell lung cancer is associated with fusion of echinoderm microtubule associated protein-like4 gene and anaplastic lymphoma kinase gene (EML4-ALK), or the non-small cell lung cancer is associated with fusion of solute carrier family 34 member 2 and ROS1 proto-oncogene 1, receptor tyrosine kinase gene (SLC34A2-ROS1).

In the above, SEQ ID NOS. 1-4 are markers for fusion of two genes, EML4 and ALK, by fusion types V3a and V3b, and SEQ ID NOS. 5-6 are markers for the fusion of two genes of SLC34A2 and ROS1.

Further, in some embodiments of the present disclose, the reagent is a primer, and the primer is selected from the group consisting of SEQ ID NOS. 7-371.

An auxiliary diagnosis method for tumor, which includes: detecting whether a biological sample derived from a subject has a circRNA having a base sequence as represented by any one of SEQ ID NOS. 1-6.

If a detection result indicates that the circRNA represented by any one of SEQ ID NOS. 1-6 exists in the biological sample, it means that the subject with a high probability of having tumor (e.g., lung cancer, for example, NSCLC).

Further, in some embodiments of the present disclosure, the method comprises detecting EML4-ALK fusion gene, comprising: detecting whether a biological sample derived from a subject has a circular RNA having a base sequence as represented by any one of SEQ ID NOS. 1-4.

Further, in some embodiments of the present disclosure, the method comprises detecting SL34A2-ROS1 fusion gene, comprising: detecting whether a biological sample derived from a subject has a circular RNA having a base sequence as represented by SEQ ID NO. 5 or 6.

Further, in some embodiments of the present disclosure, the subject is a human.

Further, in some embodiments of the present disclosure, the biological sample is blood.

Further, in some embodiments of the present disclosure, the tumor is lung cancer.

Further, in some embodiments of the present disclosure, the lung cancer is NSCLC.

A method for detecting EML4-ALK fusion gene, which includes: detecting whether a biological sample derived from a subject has a circRNA having a base sequence as represented by any one of SEQ ID NOS. 1-4.

If the detection result indicates that the circRNA represented by any one of SEQ ID NOS. 1-4 exists in the biological sample, it shows that EML4 gene and ALK gene of the subject undergo fusion.

A method for detecting SL34A2-ROS1 fusion gene, which includes: detecting whether a biological sample derived from a subject has a circRNA having a base sequence as represented by SEQ ID NO. 5 or 6.

If a detection result indicates that the circRNA represented by SEQ ID NO. 5 or 6 exists in the biological sample, it shows that SL34A2 gene and ROS1 gene of the subject undergo fusion.

BRIEF DESCRIPTION OF DRAWINGS

In order to more clearly illustrate the technical solutions of examples of the present disclosure, accompanying drawings which need to be used in the examples will be introduced below briefly, and it should be understood that the accompanying drawings below merely show some examples of the present disclosure, and therefore should not be considered as limitation to the scope, and a person ordinarily skilled in the art still could obtain other relevant accompanying drawings according to these accompanying drawings, without any inventive effort.

DETAILED DESCRIPTION OF EMBODIMENTS

Figure 1:
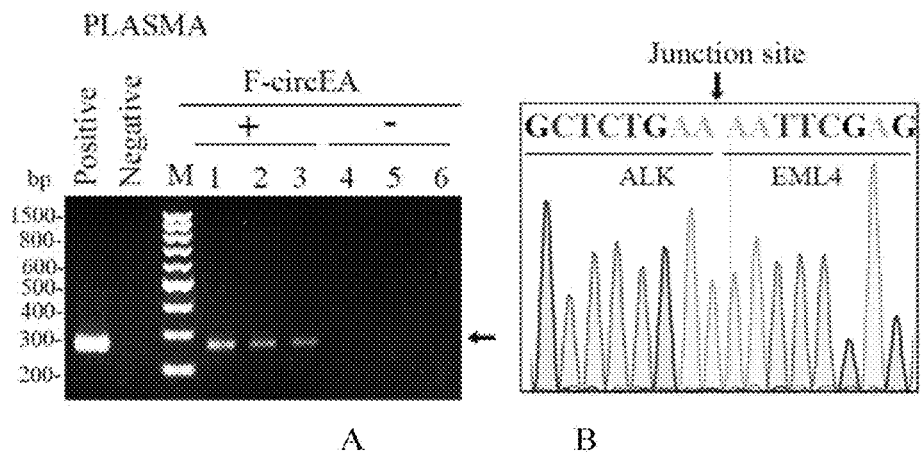
FIG. 1 shows a detection result of circRNA in plasma of patients with EML4-ALKV3a/3b fusion gene positive in Example 1 of the present disclosure (SEQ ID NO. 372 shown in panel B)

In order to make the objects, technical solutions and advantages of the examples of the present disclosure clearer, the technical solutions in the examples of the present disclosure will be described below clearly and completely. If no specific conditions are specified in the examples, they are carried out under normal conditions or conditions recommended by manufacturers. If manufacturers of reagents or apparatuses used are not specified, they are conventional products commercially available.

The features and performances of the present disclosure are further described below in detail in combination with examples.

Example 1

Three EML4-ALKV3a/3b fusion gene positive and three without EML4-ALK fusion gene positive plasma samples from lung cancer patients in West China Hospital were taken and all signed on informed consent.

CircRNA in the samples were detected through following steps:

1. Extraction of plasma RNA

1) Extracting plasma RNA: adding 750 μl of Trizol LS reagent to 250 μl of plasma to crack the plasma, fully mixing the mixture evenly, and standing at room temperature for 5 min;

2) adding 200 μl of chloroform, fully mixing them evenly, standing at room temperature for 3 min, and then centrifuging the resultant at 4° C., 12000 g for 15 min;

3) taking about 500 μl of supernatant, adding 500 μl of isopropanol, fully mixing them evenly, standing at room temperature for 10 min, and then centrifuging the resultant at 4° C., 12000 g for 10 min;

4) discarding the supernatant, retaining precipitate, adding 1 ml of 75% ethanol for washing, and then centrifuging at 4° C. and 7500 g for 5 min;

5) repeating step 4) once;

6) discarding ethanol, airing to be slightly dry, adding 11 μl of RNase-free water to dissolve RNA, and then immediately placing the resultant on ice;

7) measuring RNA concentration using 1 μl of RNA.

3. Reverse transcription system

10 μl of RNA extracted from the plasma and 2 μl of Random Decamers in RETROscript® Kit (Life, USA, article number AM1710) were mixed evenly, the mixture was heated at 85° C. for 3 min, immediately placed on ice, and then the following components were added:

| 10x RT Buffer | 2 μl |
| --- | --- |
| dNTP Mix | 4 μl |
| RNase Inhibitor | 1 μl |
| MMLV-RT | 1 μl |
| Total | 20 μl | they were mixed evenly, heated at 55° C. for 1 h, incubated at 92° C. for 10 min, and then placed on ice for subsequent use.

4. PCR system and primers:
4.1 First round of PCR

```
Sequences of primers:
EA-F01:
                                        (SEQ ID NO. 7)
5'-GCAGAGCCCTGAGTACAAGC-3';

EA-R01:
                                       (SEQ ID NO. 59)
5'-GCTTGGTTGATGATGACATCTTTATG-3'.
```

First round PCR using Vazyme Biotech, Phanta Max Super-Fidelity DNA Polymeras (p505-d1-AB) PCR kit.

The PCR system was as follows:

| 2 × Phanta Max Buffer | 25 μl |
| --- | --- |
| dNTP | 1 μl |
| The above primer EA-F01 (10 μM) | 2 μl |
| The above primer EA-R01 (10 μM) | 2 μl |
| Phanta Super-Fidelity DNA Polymerase | 1 μl |
| cDNA in step 3 | 2 μl |
| ddH$_2$O | 17 μl |
| Total | 50 μl |

PCR reaction condition:

Step 1: 95° C. for 3 min, step 2: 95° C. for 15 s, step 3: 55° C. for 15 s, step 4: 72° C. for 35 s, step 5: returning back to step 2, 40 cycles, and step 6: 72° C. for 5 min.

The theoretical length of the PCR product fragment was 503 bp or 505 bp, corresponding to F-cricEA-2A and F-cricEA-4A generated by EML4-ALK V3a/b fusion gene, respectively. However, due to the low content of F-circEA in plasma samples, bands of theoretical length may not be seen by 1.5% agarose gel electrophoresis after the first round of PCR, so following nested PCR was carried out.

4.2 Nested PCR

```
Sequences of primers used:
EA-F02:
                                       (SEQ ID NO. 8)
5'-CAACTACTGCTTTGCTGGCA-3';

EA-R02:
                                       (SEQ ID NO. 60)
5-GCATTCTTGCTTTCTGGAGTTT-3'.
```

Vazyme Biotech, Phanta Max Super-Fidelity DNA Polymeras (p505-d1-AB) PCR kit was used, and the PCR system was follows:

| 2 × Phanta Max Buffer | 25 μl |
|---|---|
| dNTP | 1 μl |
| The above primer EA-F02 (10 μM) | 2 μl |
| The above primer EA-R02 (10 μM) | 2 μl |
| Phanta Super-Fidelity DNA Polymerase | 1 μl |
| Product of first round of PCR | 2 μl |
| ddH$_2$O | 17 μl |
| Total | 50 μl |

PCR Reaction Condition:

Step 1: 95° C. for 3 min, step 2: 95° C. for 15 s, step 3: 55° C. for 15 s, step 4: 72° C. for 30 s, step 5: returning back to step 2, 40 cycles; and step 6: 72° C. for 5 min.

1.5% agarose gel electrophoresis was applied for detection. If the length of the PCR fragment was about 271 bp, the circRNA F-circEA-4A:EML4-ALK (V3a/3b) was identified in the patient's tissue; if the length of the PCR fragment was about 269 bp, the circRNA F-circEA-2A:EML4-ALK (V3a/3b) was identified in the patient's tissue. PCR products were purified and recovered for sequencing to confirm the circRNA sequence, so as to further determine that whether the patient contained the EML4-ALKfusion gene.

The result is as shown in FIG. 1. In FIG. 1: A is electrophoretogram of the PCR product of each sample, wherein: Positive represents positive control, Negative represents negative control, M represents Marker, numbers 1, 2 and 3 represent plasma samples from EML4-ALK fusion gene positive patients, and numbers 4, 5 and 6 represent plasma samples from without EML4-ALK patients; B is the sequencing map of the PCR product of tissue sample of patient No. 1, and middle arrow indicates a circularization site of the circRNA.

From the results in FIG. 1, it can be seen that the circRNA exists in the EML4-ALK positive samples (1, 2 and 3 in the figure), wherein the base sequence of linear form of the circRNA detected in sample No. 1 is as represented by SEQ ID NO. 1, with a length of 550 nt, and the fusion type F-circEA-4A:EML4-ALK (V3a).

The base sequence of linear form of the circRNA detected in sample No. 2 is as represented by SEQ ID NO. 2, with a length of 548 nt, and the fusion type F-circEA-2A:EML4-ALK (V3a);

Two circRNAs were detected from the sample No. 3, base sequences of linear form thereof are respectively as represented by SEQ ID NO.3 and SEQ ID NO. 4, the SEQ ID NO. 3 had a length of 583 nt, and the fusion type F-cricEA-4A:EML4-ALK (V3b); the SEQ ID NO. 4 had a length of 581 nt, and the fusion type F-cricEA-2A:EML4-ALK (V3b);

However, no circRNA as represented by SEQ ID NOS. 1-4 was detected from the without EML4-ALK positive samples (4/5/6 in A in FIG. 1); thus, the circRNA as represented by SEQ ID NOS. 1-4 specifically exist in EML4-ALK (V3a/b) positive patients, which can be used as a marker for judging the EML4-ALKfusion gene, and can be further used as a marker for NSCLC, particularly NSCLC especially by fusions associated with the echinoderm microtubule associated protein-like 4 (EML4) gene and anaplastic lymphoma kinase (ALK) gene (EML4-ALK).

Example 2

This example provides a method for detecting whether an ALK positive patient has an EML4-ALK fusion gene, or a fusion type thereof, specifically as follows:

1. Collecting whole blood of a patient to be tested, centrifuging the whole blood at 4° C., 1500 g for 10 min, collecting supernatant plasma, and storing the supernatant plasma at −80° C.;
2. Extracting plasma RNA as in Example 1;
3. Reverse transcription system as in Example 1;
4. PCR system and primers:
4.1 First round of PCR

```
Sequences of primers used:
EA-F01:
                                       (SEQ ID NO. 7)
5'-GCAGAGCCCTGAGTACAAGC-3';

EA-R01:
                                       (SEQ ID NO. 59)
5'-GCTTGGTTGATGATGACATCTTTATG-3'.
```

First round PCR using Vazyme Biotech, Phanta Max Super-Fidelity DNA Polymeras (p505-d1-AB) PCR kit.

The PCR system was as follows:

| 2 × Phanta Max Buffer | 25 μl |
|---|---|
| dNTP | 1 μl |
| EA-F01 (10 μM) | 2 μl |
| EA-R01 (10 μM) | 2 μl |
| Phanta Super-Fidelity DNA Polymerase | 1 μl |
| cDNA in step 3 | 2 μl |
| ddH$_2$O | 17 μl |
| Total | 50 μl |

PCR reaction condition:

Step 1: 95° C. for 3 min, step 2: 95° C. for 15 s, step 3: 55° C. for 15 s, step 4: 72° C. for 35 s, step 5: returning back to step 2, 40 cycles, and step 6: 72° C. for 5 min.

The PCR product fragment had a theoretical length of 503 bp or 505 bp.

4.2 Nested PCR

```
Sequences of primers:
EA-F02:
                                       (SEQ ID NO. 8)
5'-CAACTACTGCTTTGCTGGCA-3';
```

EA-R02:

(SEQ ID NO. 60)
5'-GCATTCTTGCTTTCTGGAGTTT-3'.

Vazyme Biotech, Phanta Max Super-Fidelity DNA Polymeras (p505-d1-AB) PCR kit was used, and the PCR system was follows:

| | |
|---|---|
| 2 × Phanta Max Buffer | 25 μl |
| dNTP | 1 μl |
| EA-F02 (10 μM) | 2 μl |
| EA-R02 (10 μM) | 2 μl |
| Phanta Super-Fidelity DNA Polymerase | 1 μl |
| Product of first round of PCR | 2 μl |
| ddH$_2$O | 17 μl |
| Total | 50 μl |

PCR Reaction Condition:

Step 1: 95° C. for 3 min, step 2: 95° C. for 15 s, step 3: 55° C. for 15 s, step 4: 72° C. for 30 s, step 5: returning back to step 2, 40 cycles, and step 6: 72° C. for 5 min. 1.5% agarose gel electrophoresis was used for detection. If the length of the PCR fragment was about 271 bp, the circRNA F-circEA-4A:EML4-ALK (V3a/3b) was identified in the patient's tissue; if the length of the PCR fragment was about 269 bp, the circRNA F-circEA-2A:EML4-ALK (V3a/3b) was identified in the patient tissue. PCR products were purified and recovered for sequencing to confirm the circRNA sequence, so as to further judge that whether the patient contained the EML4-ALKfusion gene.

In addition, it should be noted that in other examples, upstream primers in Table 1 and downstream primers in Table 2 further can be used in combination for detection, so as to determine that whether the patient has the fusion genotype of EML4-ALK v3a/b.

TABLE 1

Upstream Primers for Detecting Fusion Genotype of EML4-ALK v3a/b

| | | |
|---|---|---|
| EA-F01 | GCAGAGCCCTGAGTACAAGC | SEQ ID NO. 7 |
| EA-F02 | CAACTACTGCTTTGCTGGCA | SEQ ID NO. 8 |
| EA-F03 | AAACATCACCCTCATTCGGG | SEQ ID NO. 9 |
| EA-F04 | CAAGAATGCTACTCCCACCAA | SEQ ID NO. 10 |
| EA-F05 | TCCTCCATCAGTGACCTGAA | SEQ ID NO. 11 |
| EA-F06 | GTGTATGAAGGCCAGGTGTC | SEQ ID NO. 12 |
| EA-F07 | GAGTACAAGCTGAGCAAGCT | SEQ ID NO. 13 |
| EA-F08 | AATTCGAGCATCACCTTCTCCCCAG | SEQ ID NO. 14 |
| EA-F09 | AATTCGAGCATCACCTTCTCCC | SEQ ID NO. 15 |
| EA-F10 | AGCCCTCTTCACAACCTCTC | SEQ ID NO. 16 |
| EA-F11 | CACAACCTCTCCAAATACACAGA | SEQ ID NO. 17 |
| EA-F12 | AAACTCCAGAAAGCAAGAATGC | SEQ ID NO. 18 |
| EA-F13 | GACCATCACCAGCTGAAAAGTC | SEQ ID NO. 19 |
| EA-F14 | TGCAGAGCCCTGAGTACAAGC | SEQ ID NO. 20 |
| EA-F15 | CCAACTACTGCTTTGCTGGCA | SEQ ID NO. 21 |
| EA-F16 | CTGCAAGTGGCTGTGAAGA | SEQ ID NO. 22 |

TABLE 1-continued

Upstream Primers for Detecting Fusion Genotype of EML4-ALK v3a/b

| | | |
|---|---|---|
| EA-F17 | GTGAAGACGCTGCCTGAA | SEQ ID NO. 23 |
| EA-F18 | CCATCATGACCGACTACAAC | SEQ ID NO. 24 |
| EA-F19 | TGTATGAAGGCCAGGTGT | SEQ ID NO. 25 |
| EA-F20 | CTGAGTACAAGCTGAGCAAG | SEQ ID NO. 26 |
| EA-F21 | CATCAGTGACCTGAAGGAG | SEQ ID NO. 27 |
| EA-F22 | GAAGACGCTGCCTGAAG | SEQ ID NO. 28 |
| EA-F23 | TGCAAGTGGCTGTGAAG | SEQ ID NO. 29 |
| EA-F24 | CCTGAAGTGTGCTCTGAAA | SEQ ID NO. 30 |
| EA-F25 | CCCAACTACTGCTTTGCT | SEQ ID NO. 31 |
| EA-F26 | CGCTGCCTGAAGTGTGCTCTGAAAA | SEQ ID NO. 32 |
| EA-F27 | GCTGCCTGAAGTGTGCTCTGAAAAT | SEQ ID NO. 33 |
| EA-F28 | CTGCCTGAAGTGTGCTCTGAAAATT | SEQ ID NO. 34 |
| EA-F29 | TGCCTGAAGTGTGCTCTGAAAATTC | SEQ ID NO. 35 |
| EA-F30 | GCCTGAAGTGTGCTCTGAAAATTCG | SEQ ID NO. 36 |
| EA-F31 | CCTGAAGTGTGCTCTGAAAATTCGA | SEQ ID NO. 37 |
| EA-F32 | CTGAAGTGTGCTCTGAAAATTCGAG | SEQ ID NO. 38 |
| EA-F33 | TGAAGTGTGCTCTGAAAATTCGAGC | SEQ ID NO. 39 |
| EA-F34 | GAAGTGTGCTCTGAAAATTCGAGCA | SEQ ID NO. 40 |
| EA-F35 | AAGTGTGCTCTGAAAATTCGAGCAT | SEQ ID NO. 41 |
| EA-F36 | AGTGTGCTCTGAAAATTCGAGCATC | SEQ ID NO. 42 |
| EA-F37 | GTGTGCTCTGAAAATTCGAGCATCA | SEQ ID NO. 43 |
| EA-F38 | TGTGCTCTGAAAATTCGAGCATCAC | SEQ ID NO. 44 |
| EA-F39 | GTGCTCTGAAAATTCGAGCATCACC | SEQ ID NO. 45 |
| EA-F40 | TGCTCTGAAAATTCGAGCATCACCT | SEQ ID NO. 46 |
| EA-F41 | GCTCTGAAAATTCGAGCATCACCTT | SEQ ID NO. 47 |
| EA-F42 | CTCTGAAAATTCGAGCATCACCTTC | SEQ ID NO. 48 |
| EA-F43 | TCTGAAAATTCGAGCATCACCTTCT | SEQ ID NO. 49 |
| EA-F44 | CTGAAAATTCGAGCATCACCTTCTC | SEQ ID NO. 50 |
| EA-F45 | TGAAAATTCGAGCATCACCTTCTCC | SEQ ID NO. 51 |
| EA-F46 | GAAAATTCGAGCATCACCTTCTCCC | SEQ ID NO. 52 |
| EA-F47 | TGTGCTCTGAAAATTCGAGCAT | SEQ ID NO. 53 |
| EA-F48 | GCTCTGAAAATTCGAGCATCACCTTC | SEQ ID NO. 54 |
| EA-F49 | GCTCTGAAAATTCGAGCATCAC | SEQ ID NO. 55 |
| EA-F50 | AGTGTGCTCTGAATTCGAGC | SEQ ID NO. 56 |
| EA-F51 | GCTCTGAATTCGAGCATCACC | SEQ ID NO. 57 |
| EA-F52 | GCCTGAAGTGTGCTCTGAATT | SEQ ID NO. 58 |

TABLE 2

Downstream Primers for Detecting Fusion Genotype of EML4-ALK v3a/b

| | | |
|---|---|---|
| EA-R01 | GCTTGGTTGATGATGACATCTTTATG | SEQ ID NO. 59 |
| EA-R02 | GCATTCTTGCTTTCTGGAGTTT | SEQ ID NO. 60 |
| EA-R03 | TTGTAGTCGGTCATGATGGTC | SEQ ID NO. 61 |
| EA-R04 | GGAGAAGGTGATGCTCGAATT | SEQ ID NO. 62 |
| EA-R05 | GCTTGCTCAGCTTGTACTCA | SEQ ID NO. 63 |
| EA-R06 | TTCAGGTCACTGATGGAGGA | SEQ ID NO. 64 |
| EA-R07 | TTTGCTTGGTTGATGATGACATC | SEQ ID NO. 65 |
| EA-R08 | TTCAGAGCACACTTCAGGCAGC | SEQ ID NO. 66 |
| EA-R09 | TCTGTGTATTTGGAGAGGTTGTGA | SEQ ID NO. 67 |
| EA-R10 | TCTGTGTATTTGGAGAGGTTGTG | SEQ ID NO. 68 |
| EA-R11 | GCTTGGTTGATGATGACATCTTTATGC | SEQ ID NO. 69 |
| EA-R12 | TGCCAGCAAAGCAGTAGTTG | SEQ ID NO. 70 |
| EA-R13 | CACCTGGCCTTCATACACCT | SEQ ID NO. 71 |
| EA-R14 | TCTTCACAGCCACTTGCAG | SEQ ID NO. 72 |
| EA-R15 | TTCAGGCAGCGTCTCAC | SEQ ID NO. 73 |
| EA-R16 | GTCGTTTTATGCTTTTGGTGGGAGTA | SEQ ID NO. 74 |
| EA-R17 | GATGGTCGTTTTATGCTTTTGGTG | SEQ ID NO 75 |
| EA-R18 | TCTGGAGTTTGTCTGTGTATTT | SEQ ID NO. 76 |
| EA-R19 | GAGAAGGTGATGCTCGAATTT | SEQ ID NO. 77 |
| EA-R20 | TTTGTCTGTGTATTTGGAGAGG | SEQ ID NO. 78 |
| EA-R21 | GAGTAGCATTCTTGCTTTCTG | SEQ ID NO. 79 |
| EA-R22 | TTTCCCAAGAATTATGTGACTTT | SEQ ID NO. 80 |
| EA-R23 | TATTTGGAGAGGTTGTGAAGAG | SEQ ID NO. 81 |
| EA-R24 | GGTGGGAGTAGCATTCTTG | SEQ ID NO. 82 |
| EA-R25 | TCTTGCTTTCTGGAGTTTGT | SEQ ID NO. 83 |
| EA-R26 | TTTTCAGAGCACACTTCAGGCAGCG | SEQ ID NO. 84 |
| EA-R27 | ATTTTCAGAGCACACTTCAGGCAGC | SEQ ID NO. 83 |
| EA-R28 | AATTTTCAGAGCACACTTCAGGCAG | SEQ ID NO. 86 |
| EA-R29 | GAATTTTCAGAGCACACTTCAGGCA | SEQ ID NO. 87 |
| EA-R30 | CGAATTTTCAGAGCACACTTCAGGC | SEQ ID NO. 88 |
| EA-R31 | TCGAATTTTCAGAGCACACTTCAGG | SEQ ID NO. 89 |
| EA-R32 | CTCGAATTTTCAGAGCACACTTCAG | SEQ ID NO. 90 |
| EA-R33 | GCTCGAATTTTCAGAGCACACTTCA | SEQ ID NO. 91 |
| EA-R34 | TGCTCGAATTTTCAGAGCACACTTC | SEQ ID NO. 92 |
| EA-R35 | ATGCTCGAATTTTCAGAGCACACTT | SEQ ID NO. 93 |
| EA-R36 | GATGCTCGAATTTTCAGAGCACACT | SEQ ID NO. 94 |
| EA-R37 | TGATGCTCGAATITTCAGAGCACAC | SEQ ID NO. 95 |
| EA-R38 | GTGATGCTCGAATTTTCAGAGCACA | SEQ ID NO. 96 |
| EA-R39 | GGTGATGCTCGAATTTTCAGAGCAC | SEQ ID NO. 97 |
| EA-R40 | AGGTGATGCTCGAATTTTCAGAGCA | SEQ ID NO. 98 |
| EA-R41 | AAGGTGATGCTCGAATTTTCAGAGC | SEQ ID NO. 99 |
| EA-R42 | GAAGGTGATGCTCGAATTFTCAGAG | SEQ ID NO. 100 |
| EA-R43 | AGAAGGTGATGCTCGAATTTTCAGA | SEQ ID NO. 101 |
| EA-R44 | GAGAAGGTGATGCTCGAATTTTCAG | SEQ ID NO. 102 |
| EA-R45 | GGAGAAGGTGATGCTCGAATTTTCA | SEQ ID NO. 103 |
| EA-R46 | TGGGGAGAAGGTGATGCTCGAATTTTC | SEQ ID NO. 104 |
| EA-R47 | ATGCTCGAATTTTCAGAGCACA | SEQ ID NO. 105 |
| EA-R48 | AGGTGATGCTCGAATTTTCAGAG | SEQ ID NO. 106 |
| EA-R49 | GTGATGCTCGAATTTTCAGAGC | SEQ ID NO. 107 |
| EA-R50 | GCTCGAATTCAGAGCACACT | SEQ ID NO. 108 |
| EA-R51 | GGTGATGCTCGAATTCAGAGC | SEQ ID NO. 109 |
| EA-R52 | AATTCAGAGCACACTTCAGGC | SEQ ID NO. 110 |

Example 3

The present example provides a method for detecting whether a lung cancer patient has an SLC34A2-ROS1 fusion gene, specifically as follows:

Taking 4 plasma samples of lung cancer patients (wherein two are from patients with SLC34A2-ROS1 fusion gene, and two are from patients without SLC34A2-ROS1 fusion gene), wherein all of the patients signed on informed consent.

1. Extracting plasma RNA as in Example 1;
2. Reverse transcription system as in Example 1;
3. PCR system and primers:

```
Sequences of primers used:
G103:
                                    (SEQ ID NO. 243)
5'-TCCTGAAGAGTGGGTAGGTT-3';

WK23:
                                    (SEQ ID NO. 113)
5'-TGTATGAAGGAACAGCAGTGG-3';

WK24:
                                    (SEQ ID NO. 114)
5'-GTGAAGATTGGAGACTTTGGAC-3'.
```

PCR reaction system:
System 1 (WK24/G103/detecting CF1):

| | |
|---|---|
| 2 × Phanta Max Buffer | 25 μl |
| dNTP | 1 μl |
| WK24 (10 μM) | 2 μl |
| G103 (10 μM) | 2 μl |
| Phanta Max Super-Fidelity DNA Polymerase | 1 μl |
| cDNA | 1 μl |
| ddH₂O | 18 μl |
| Total | 50 μl |

System 2 (WK23/G103 detecting CF2):

| | |
|---|---|
| 2 × Phanta Max Buffer | 25 μl |
| dNTP | 1 μl |
| WK23 (10 μM) | 2 μl |
| G103 (10 μM) | 2 μl |
| Phanta Max Super-Fidelity DNA Polymerase | 1 μl |
| cDNA | 1 μl |
| ddH₂O | 18 μl |
| Total | 50 μl |

PCR Reaction Condition:

Step 1: 95° C. for 3 min; step 2: 95° C. for 15 s; step 3: 61° C. for 15s; step 4:72° C. for 2 min; step 5: returning back to step 2, 44 cycles; and step 6: 72° C. for 5 min.

4. Electrophoresis and sequencing of PCR products:

1.5% agarose gel electrophoresis was used for detection, and PCR products were purified and recovered for sequencing.

Figure 2:
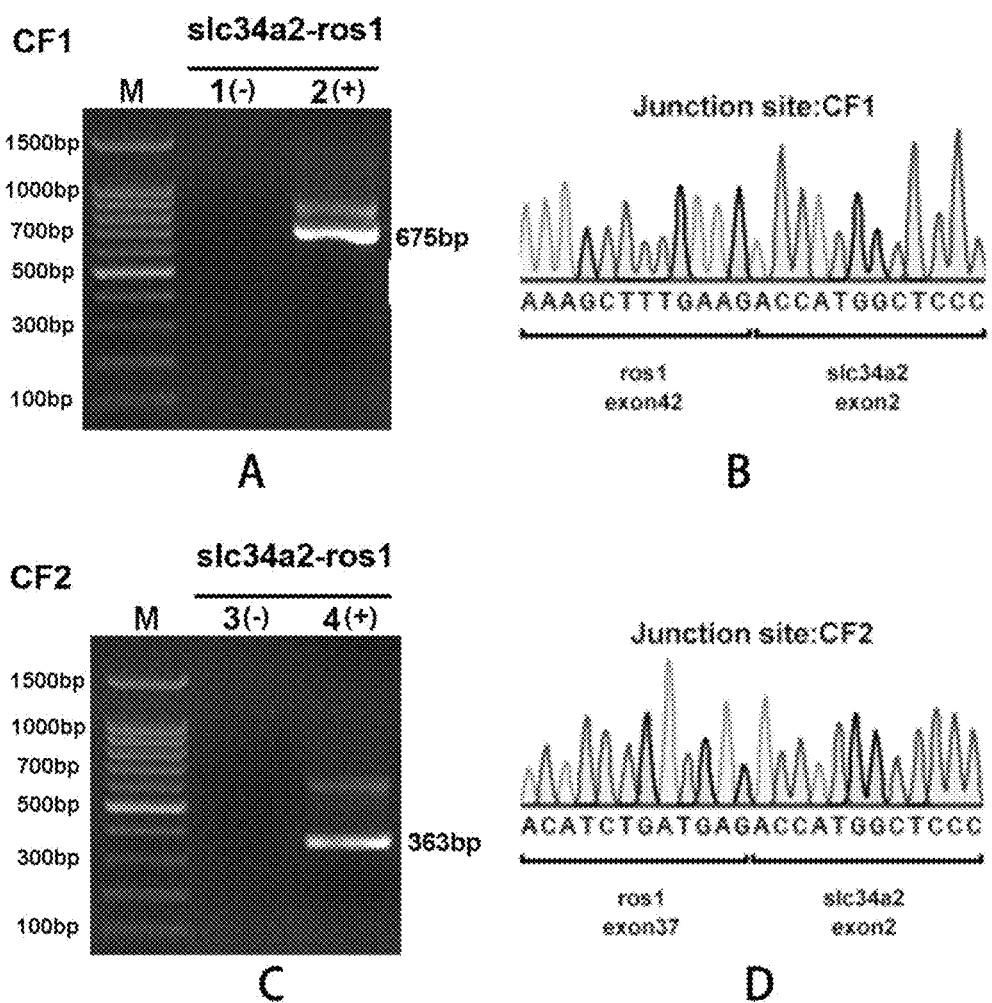
FIG. 2 shows a detection result of circRNA in plasma of patients with SLC34A2-ROS1 fusion gene positive in Example 2 of the present disclosure (SEQ ID NO. 373 shown in panel B; SEQ ID NO. 374 shown in panel D)

The result is as shown in FIG. 2. In A and C in FIG. 2: – represents negative control, + represents positive control, M represents Marker, numbers 1 and 2 represent patient plasma samples tested for CF1, and 3 and 4 represent patient plasma samples tested for CF2. Band D in FIG. 2 are sequencing charts of patient sample Nos. 2 and 4, respectively, and the middle arrow indicates a site of circularization of the circRNA.

As can be seen from FIG. 2, the circRNA exists in the SLC34A2-ROS1 positive samples (2 in A in FIGS. 2 and 4 in C in FIG. 2), wherein the circRNA detected in sample No. 2 has a base sequence as presented by SEQ ID NO. 5, with a length of 1867 bp, and fusion type CF1; the circRNA detected in sample No. 4 has a base sequence as presented by SEQ ID NO. 6, with a length of 830 bp, and fusion type CF2; while no such circRNA as represented by SEQ ID NOS. 5-6 was detected from the sample without SLC34A2-ROS1 positive: it thus indicates that the circRNA represented by SEQ ID NOS. 5-6 specifically exists in SLC34A2-ROS1 fusion positive patients, which can be used as a marker for confirming SLC34A2-ROS1 fusion genes, and can be further used as a marker for NSCLC, particularly NSCLC caused by the fusion of solute carrier family 34 member 2 and ROS proto-oncogene 1,receptor tyrosine kinase gene (SLC34A2-ROS1).

Example 4

The present example provides a method for detecting whether a circRNA exists in plasma RNA of a ROS1 positive patient (a patient having SLC34A2-ROS1 fusion gene). The method is specifically as follows:

1. Collecting whole blood of a patient, centrifuging the whole blood at 4° C. and 1500 g for 10 min, collecting supernatant plasma, and storing the supernatant plasma at −80° C.;
2. Extracting plasma RNA as in Example 1;
3. Reverse transcription system as in Example 1;
4. PCR system and primers:

```
Sequences of primers used:
G103:
                                      (SEQ ID NO. 243)
5'-TCCTGAAGAGTGGGTAGGTT-3';

G102:
                                      (SEQ ID NO. 111)
5'-TTCCAACCCAAGAGGAGATTG-3';

G106:
                                      (SEQ ID NO. 112)
5'-CAGTGGGAGAAAGCTGAAGATAA-3'.
```

PCR reaction system:

System 1 (G102/G103):

| | |
|---|---|
| 2 × Phanta Max Buffer | 25 μl |
| dNTP | 1 μl |
| G102 (10 μM) | 2 μl |
| G103 (10 μM) | 2 μl |
| Phanta Max Super-Fidelity DNA Polymerase | 1 μl |
| cDNA | 1 μl |
| ddH₂O | 18 μl |
| Total | 50 μl |

System 2 (G103/G106):

| | |
|---|---|
| 2 × Phanta Max Buffer | 25 μl |
| dNTP | 1 μl |
| G103 (10 μM) | 2 μl |
| G106 (10 μM) | 2 μl |
| Phanta Max Super-Fidelity DNA Polymerase | 1 μl |
| cDNA | 1 μl |
| ddH₂O | 18 μl |
| Total | 50 μl |

PCR Reaction Condition:

Step 1: 95° C. for 3 min; step 2: 95° C. for 15 s; step 3: 61° C. for 15 s; step 4: 72° C. for 2 min; step 5: returning back to step 2, 44 cycles; and step 6: 72° C. for 5 min.

5. Electrophoresis of PCR Product

Figure 3:
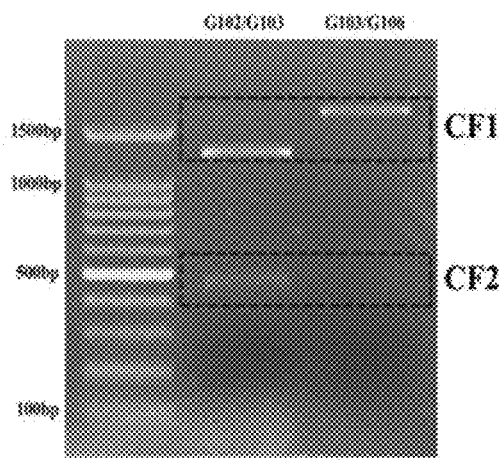
FIG. 3 shows a PCR result of determining the type of SLC34A2-ROS1 fusion gene by means of combining primers of SEQ ID NO. 111/SEQ ID NO. 243 and SEQ ID NO. 243/SEQ ID NO. 112 in Example 3 of the present disclosure.

An electrophoresis result is as shown in FIG. 3. If the length of the PCR fragment with primer G103 (SEQ ID NO. 243)/G102 (SEQ ID NO. 111) after 1.5% agarose gel electrophoresis was 1184 bp, it could be identified that the plasma of the patient contained CF1.

If the length of the PCR fragment with primer G103 (SEQ ID NO. 243)/G106 (SEQ ID NO. 112) after agarose gel electrophoresis was 1659 bp, it could be identified that the plasma of the patient contained CF1.

If the length of the PCR fragment with primer G103 (SEQ ID NO. 243)/G102 (SEQ ID NO. 111) after agarose gel electrophoresis was 456 bp, it could be identified that the plasma of the patient contained CF2.

Figure 4:
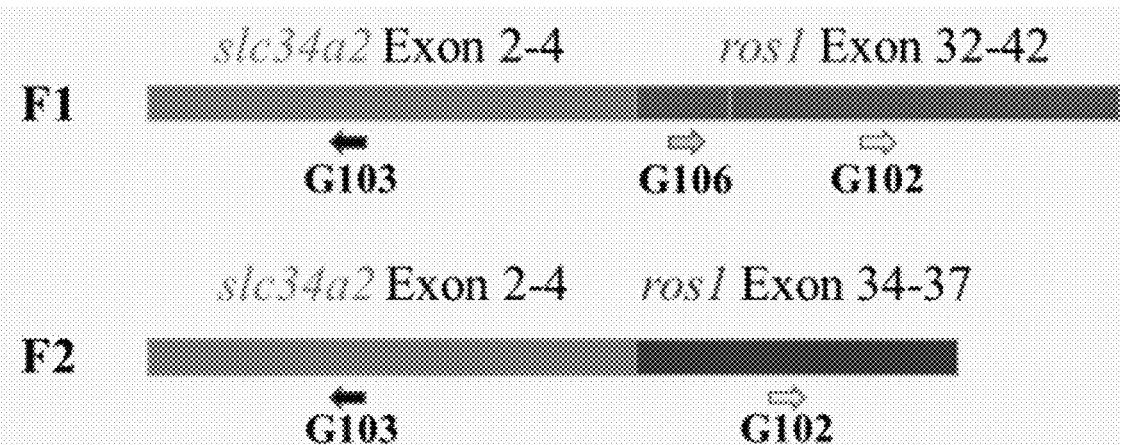
FIG. 4 is a structural schematic diagram of positions and structures of the primers SEQ ID NO. 243, SEQ ID NO. 111 and SEQ ID NO. 112 corresponding to different fusion types of SLC34A2 and ROS1 in Example 3 of the present disclosure.

Positions of G103 (SEQ ID NO. 243), G102 (SEQ ID NO. 111) and G106 (SEQ ID NO. 112) corresponding to different fusion types of SLC34A2 and ROS1 are as shown in FIG. 4. In FIG. 4, F1 represents fusion of SLC34A2 exons 2-4 with exons 32-42 of ROS1 gene; F2 represents fusion of ROS1 with exons 34-37 of the ROS1 gene; due to different positions of the PCR primer designed, it can be determined that an amplification product of G103 (SEQ ID NO. 243)/G106 (SEQ ID NO. 112) is from a circRNA in a fusion type F1, namely CF1; while an amplification product of G103 (SEQ ID NO. 243)/G102 SEQ ID NO. 111) is from a circRNA in a fusion type F2, namely CF2.

Besides, PCR also can be carried out with combinations of upstream primers set forth in Table 3 and downstream primers set forth in Table 4 to determine that whether the patient has the fusion genotype of SLC34A2-ROS1.

TABLE 3

Upstream Primers for Detecting Fusion Genotype of SLC34A2-ROS1

| | | |
|---|---|---|
| G102 | TTCCAACCCAAGAGGAGATTG | SEQ ID NO. 111 |
| G106 | CAGTGGGAGAAAGCTGAAGATAA | SEQ ID NO. 112 |
| WK23 | TGTATGAAGGAACAGCAGTGG | SEQ ID NO. 113 |
| WK24 | GTGAAGATTGGAGACTTTGGAC | SEQ ID NO. 114 |
| F01 | CATACTCTTCCAACCCAAGAGG | SEQ ID NO. 115 |
| F02 | CTTATCCAGCTCATTCCAACCT | SEQ ID NO. 116 |
| F03 | CTTTACTCACCTTGGTTGACCT | SEQ ID NO. 117 |
| F04 | AGTGTATGAAGGAACAGCAGTG | SEQ ID NO. 118 |
| F05 | GAGATGAAGCAAACAACAGTGG | SEQ ID NO. 119 |
| F06 | GTATGAAGGAACAGCAGTGGA | SEQ ID NO. 120 |
| F07 | AGAGAGAGACACCAAAGGGA | SEQ ID NO. 121 |
| F08 | CAATCCCACTGACCTTTGTCT | SEQ ID NO. 122 |
| F09 | CACAGACCAGGAGAAGATTGAA | SEQ ID NO. 123 |
| F10 | GATATTCTTAGTAGCGCCTTCCA | SEQ ID NO. 124 |
| F11 | CATAAATGAAAGCTTTGAAGACCAT | SEQ ID NO. 125 |
| F12 | TCATAAATGAAAGCTTTGAAGACCA | SEQ ID NO. 126 |
| F13 | GTCATAAATGAAAGCTTTGAAGACC | SEQ ID NO. 127 |
| F14 | AGTCATAAATGAAAGCTTTGAAGAC | SEQ ID NO. 128 |
| F15 | ATAAATGAAAGCTTTGAAGACCATG | SEQ ID NO. 129 |
| F16 | TAAATGAAAGCTTTGAAGACCATGG | SEQ ID NO. 130 |
| F17 | AAATGAAAGCTTTGAAGACCATGGC | SEQ ID NO. 131 |
| F18 | AATGAAAGCTTTGAAGACCATGGCT | SEQ ID NO. 132 |
| F19 | ATGAAAGCTTTGAAGACCATGGCTC | SEQ ID NO. 133 |
| F20 | TGAAAGCTTTGAAGACCATGGCTCC | SEQ ID NO. 134 |
| F21 | GAAAGCTTTGAAGACCATGGCTCCC | SEQ ID NO. 135 |
| F22 | AAAGCTTTGAAGACCATGGCTCCCT | SEQ ID NO. 136 |
| F23 | AAGCTTTGAAGACCATGGCTCCCTG | SEQ ID NO. 137 |
| F24 | AGCTTTGAAGACCATGGCTCCCTGG | SEQ ID NO. 138 |
| F25 | GCTTTGAAGACCATGGCTCCCTGGC | SEQ ID NO. 139 |
| F26 | CTTTGAAGACCATGGCTCCCTGGCC | SEQ ID NO. 140 |
| F27 | TTTGAAGACCATGGCTCCCTGGCCT | SEQ ID NO. 141 |
| F28 | TTGAAGACCATGGCTCCCTGGCCTG | SEQ ID NO. 142 |
| F29 | TGAAGACCATGGCTCCCTGGCCTGA | SEQ ID NO. 143 |
| F30 | GAAGACCATGGCTCCCTGGCCTGAA | SEQ ID NO. 144 |
| F31 | AAGACCATGGCTCCCTGGCCTGAAT | SEQ ID NO. 145 |
| F32 | AGACCATGGCTCCCTGGCCTGAATT | SEQ ID NO. 146 |
| F33 | CTGAAGGAGGCACATCTGATGAGAC | SEQ ID NO. 147 |
| F34 | TGAAGGAGGCACATCTGATGAGACC | SEQ ID NO. 148 |
| F35 | GAAGGAGGCACATCTGATGAGACCA | SEQ ID NO. 149 |
| F36 | AAGGAGGCACATCTGATGAGACCAT | SEQ ID NO. 150 |
| F37 | AGGAGGCACATCTGATGAGACCATG | SEQ ID NO. 151 |
| F38 | GGAGGCACATCTGATGAGACCATGG | SEQ ID NO. 152 |
| F39 | GAGGCACATCTGATGAGACCATGGC | SEQ ID NO. 153 |
| F40 | AGGCACATCTGATGAGACCATGGCT | SEQ ID NO. 154 |
| F41 | GGCACATCTGATGAGACCATGGCTC | SEQ ID NO. 155 |
| F42 | GCACATCTGATGAGACCATGGCTCC | SEQ ID NO. 156 |
| F43 | CACATuTGATGAGACCATGGCTCCC | SEQ ID NO. 157 |
| F44 | ACATCTGATGAGACCATGGCTCCCT | SEQ ID NO. 158 |
| F45 | CATCTGATGAGACCATGGCTCCCTG | SEQ ID NO. 159 |
| F46 | ATCTGATGAGACCATGGCTCCCTGG | SEQ ID NO. 160 |
| F47 | TCTGATGAGACCATGGCTCCCTGGC | SEQ ID NO. 161 |
| F48 | CTGATGAGACCATGGCTCCCTGGCC | SEQ ID NO. 162 |
| F49 | TGATGAGACCATGGCTCCCTGGCCT | SEQ ID NO. 163 |
| F50 | GATGAGACCATGGCTCCCTGGCCTG | SEQ ID NO. 164 |
| F51 | ATGAGACCATGGCTCCCTGGCCTGA | SEQ ID NO. 165 |
| F52 | TGAGACCATGGCTCCCTGGCCTGAA | SEQ ID NO. 166 |
| F53 | GAGACCATGGCTCCCTGGCCTGAAT | SEQ ID NO. 167 |
| F54 | AAGACCATGGCTCCCTGGCCTGAATT | SEQ ID NO. 168 |
| F55 | GATGGATGGAATCTTCACTACTC | SEQ ID NO. 169 |
| F56 | CTCAAGAACCCGACCAAAG | SEQ ID NO. 170 |
| F57 | CTTAAATAGCATTTATAAGTCCAGAGATG | SEQ ID NO. 171 |
| F58 | CAGCCTTATCCAGCTCATTC | SEQ ID NO. 172 |
| F59 | TGTGGAATTTAATGACCCAGT | SEQ ID NO. 173 |
| F60 | GACCAACTTCAGTTATTCAGAAAT | SEQ ID NO. 174 |
| F61 | TGAAGCAAACAACAGTGGAG | SEQ ID NO. 175 |
| F62 | TTCATAGAATTCAGGACCAACT | SEQ ID NO. 176 |
| F63 | AGTGCTGGGCTCAAGAA | SEQ ID NO. 177 |
| F64 | ACCAAGAAATTGTCCTGATGAT | SEQ ID NO. 178 |
| F65 | TGCAAACAGGAGGGAGA | SEQ ID NO. 179 |
| F66 | CTGGAGCCACCAAGAAAT | SEQ ID NO. 180 |
| F67 | ATTCAGGACCAACTTCAGTTAT | SEQ ID NO. 181 |
| F68 | GTCCTGATGATCTGTGGAATTTA | SEQ ID NO. 182 |
| F69 | ACTCAATCTGATGTATGGTCTTT | SEQ ID NO. 183 |
| F70 | CAAACAACAGTGGAGTCATAAAT | SEQ ID NO. 184 |
| F71 | GTCCAGAGATGAAGCAAACA | SEQ ID NO. 185 |
| F72 | CAGCTAGAAATTGCCTTGTTTC | SEQ ID NO. 186 |
| F73 | GGAGTTTGTCTGCTGAATGA | SEQ ID NO. 187 |

TABLE 3-continued

Upstream Primers for Detecting Fusion Genotype of SLC34A2-ROS1

| | | |
|---|---|---|
| F74 | CCTTGTAGACCTGTGTGTAGA | SEQ ID NO. 188 |
| F75 | GTGTCTACTTGGAACGGATG | SEQ ID NO. 189 |
| F76 | CAGGGATCTGGCAGCTA | SEQ ID NO. 190 |
| F77 | CCTTGGTTGACCTTGTAGAC | SEQ ID NO. 191 |
| F78 | AGGCTGTGTCTACTTGGA | SEQ ID NO. 192 |
| F79 | GCATTTCATTCACAGGGATCT | SEQ ID NO. 193 |
| F80 | GAACGGATGCATTTCATTCAC | SEQ ID NO. 194 |
| F81 | GGATCTGGCAGCTAGAAATTG | SEQ ID NO. 195 |
| F82 | GTGAAAGACTATACCAGTCCAC | SEQ ID NO. 196 |
| F83 | GGGAGGAGACCTTCTTACTT | SEQ ID NO. 197 |
| F84 | TGTTTCCGTGAAAGACTATACC | SEQ ID NO. 198 |
| F85 | GGAGAAGTGTATGAAGGAACAG | SEQ ID NO. 199 |
| F86 | TTACAATCCCACTGACCTTTG | SEQ ID NO. 200 |
| F87 | GGAGTTGGAAGTGGAGAAATC | SEQ ID NO. 201 |
| F88 | AAAGTGCCAAGGAAGGG | SEQ ID NO. 202 |
| F89 | GACTTTGAAGAAGGGTTCCA | SEQ ID NO. 203 |
| F90 | TGGAAGTGGAGAAATCAAAGTAG | SEQ ID NO. 204 |
| F91 | TAGCAGTGAAGACTTTGAAGAA | SEQ ID NO. 205 |
| F92 | GAAATCAAAGTAGCAGTGAAGAC | SEQ ID NO. 206 |
| F93 | GAGCCTTTGGAGAAGTGTATG | SEQ ID NO. 207 |
| F94 | AGTGGAGCCTTTGGAGAA | SEQ ID NO. 208 |
| F95 | CAGTGGACATCTTAGGAGTTG | SEQ ID NO. 209 |
| F96 | GAACAGCAGTGGACATCTT | SEQ ID NO. 210 |
| F97 | CATCTTAGGAGTTGGAAGTGG | SEQ ID NO. 211 |
| F98 | CTGGCTAATGCCTGCTATG | SEQ ID NO. 212 |
| F99 | GTGGGAGAAAGCTGAAGATAA | SEQ ID NO. 213 |
| F100 | GGATCCTGCAGTAGTGTTTG | SEQ ID NO. 214 |
| F101 | ACCAGGCATTCCCAAATTAC | SEQ ID NO. 215 |
| F102 | AAGCTGAAGATAATGGATGTAGAA | SEQ ID NO. 216 |
| F103 | TTCAGAGTAGTAGCTGCAAATAA | SEQ ID NO. 217 |
| F104 | AGTAGCTGCAAATAATCTAGGG | SEQ ID NO. 218 |
| F105 | AACCAGAATTTAAGGTGGAAGA | SEQ ID NO. 219 |
| F106 | GGGTTTGGTGAATATAGTGGAA | SEQ ID NO. 220 |
| F107 | CCCAAATTACTAGAAGGGAGTAAA | SEQ ID NO. 221 |
| F108 | TTCAATACAGTGGGAGAAAGC | SEQ ID NO. 222 |
| F109 | GTGAATATAGTGGAATCAGTGAGA | SEQ ID NO. 223 |
| F110 | GCAAATAATCTAGGGTTTGGTG | SEQ ID NO. 224 |
| F111 | TCCCAAATAAACCAGGCATTC | SEQ ID NO. 225 |
| F112 | CAGTAGTGTTTGCACATGGA | SEQ ID NO. 226 |
| F113 | GAGATAAGAAAGAGCACTTCAAATAA | SEQ ID NO. 227 |
| F114 | GGATACCAGAAACAAGTTTCATAC | SEQ ID NO. 228 |
| F115 | GAAAGGAATATTTCAGTTCAGAGTAG | SEQ ID NO. 229 |
| F116 | GAATTTAAGGTGGAAGATGACATTTA | SEQ ID NO. 230 |
| F117 | GCATTCCCAAATTACTAGAAGG | SEQ ID NO. 231 |
| F118 | TCCTTGAGATAAGAAAGAGCAC | SEQ ID NO. 232 |
| F119 | TGCACATGGAAGTCCAAA | SEQ ID NO. 233 |
| F120 | ATAGTTGGAATATTTCTGGTTGT | SEQ ID NO. 234 |
| F121 | GCACTTCAAATAATTTACAGAACCA | SEQ ID NO. 235 |
| F122 | AGATGACATTTAATGGATCCTG | SEQ ID NO. 236 |
| F123 | AGTCATAAATGAAAGCTTTGAAGACCATG | SEQ ID NO. 237 |
| F124 | TTGAAGACCATGGCTCCCTG | SEQ ID NO. 238 |
| F125 | AAAGCTTTGAAGACCATGGCTC | SEQ ID NO. 239 |
| F126 | CACATCTGATGAGACCATGGCTC | SEQ ID NO. 240 |
| F127 | CTGATGAGACCATGGCTCC | SEQ ID NO. 241 |
| F128 | ATGAGACCATGGCTCCCTG | SEQ ID NO. 242 |

TABLE 4

Downstream Primers for Detecting Fusion Genotype of SLC34A2-ROS1

| | | |
|---|---|---|
| G103 | TCCTGAAGAGTGGGTAGGTT | SEQ ID NO. 243 |
| R01 | TTTATTTGGGACTCCAGCTCC | SEQ ID NO. 244 |
| R02 | TCATACACTTCTCCAAAGGCTC | SEQ ID NO. 245 |
| R03 | CAATCTCCTCTTGGGTTGGAA | SEQ ID NO. 246 |
| R04 | CTAAGAATATCCAGGGAGCACAC | SEQ ID NO. 247 |
| R05 | GGATAAGGCTGATGACCAAGAG | SEQ ID NO. 248 |
| R06 | TCAATCTCCTCTTGGGTTGGAA | SEQ ID NO. 249 |
| R07 | TATCAGTGTAGCCGTGGAGTA | SEQ ID NO. 250 |
| R08 | AATCATCTCCAACCAGCTGG | SEQ ID NO. 251 |
| R09 | TAAGATGTCCACTGCTGTTCC | SEQ ID NO. 252 |
| R10 | AATCTTCCCTTTGGTGTCTCTC | SEQ ID NO. 253 |
| R11 | ATGGTCTTCAAAGCTTTCATTTATG | SEQ ID NO. 254 |
| R12 | TGGTCTTCAAAGCTTTCATTTATGA | SEQ ID NO. 255 |
| R13 | GGTCTTCAAAGCTTTCATTTATGAC | SEQ ID NO. 256 |
| R14 | GTCTTCAAAGCTTTCATTTATGACT | SEQ ID NO. 257 |
| R15 | CATGGTCTTCAAAGCTTTCATTTTAT | SEQ ID NO. 258 |
| R16 | CCATGGTCTTCAAAGCTTTCATTTA | SEQ ID NO. 259 |
| R17 | GCCATGGTCTTCAAAGCTTTCATTT | SEQ ID NO. 260 |

TABLE 4-continued

Downstream Primers for Detecting Fusion Genotype of SLC34A2-ROS1

| | | |
|---|---|---|
| R18 | AGCCATGGTCTTCAAAGCTTTCATT | SEQ ID NO. 261 |
| R19 | GAGCCATGGTCTTCAAAGCTTTCAT | SEQ ID NO. 262 |
| R20 | GGAGCCATGGTCTTCAAAGCTTTCA | SEQ ID NO. 263 |
| R21 | GGGAGCCATGGTCTTCAAAGCTTTC | SEQ ID NO. 264 |
| R22 | AGGGAGCCATGGTCTTCAAAGCTTT | SEQ ID NO. 265 |
| R23 | CAGGGAGCCATGGTCTTCAAAGCTT | SEQ ID NO. 266 |
| R24 | CCAGGGAGCCATGGTCTTCAAAGCT | SEQ ID NO. 267 |
| R25 | GCCAGGGAGCCATGGTCTTCAAAGC | SEQ ID NO. 268 |
| R26 | GGCCAGGGAGCCATGGTCTTCAAAG | SEQ ID NO. 269 |
| R27 | AGGCCAGGGAGCCATGGTCTTCAAA | SEQ ID NO. 270 |
| R28 | CAGGCCAGGGAGCCATGGTCTTCAA | SEQ ID NO. 271 |
| R29 | TCAGGCCAGGGAGCCATGGTCTTCA | SEQ ID NO. 272 |
| R30 | ATTCAGGCCAGGGAGCCATGGTCTT | SEQ ID NO. 273 |
| R31 | TTCAGGCCAGGGAGCCATGGTCTTC | SEQ ID NO. 274 |
| R32 | AATTCAGGCCAGGGAGCCATGGTCT | SEQ ID NO. 275 |
| R33 | GTCTCATCAGATGTGCCTCCTTCAG | SEQ ID NO. 276 |
| R34 | GGTCTCATCAGATGTGCCTCCTTCA | SEQ ID NO. 277 |
| R35 | TGGTCTCATCAGATGTGCCTCCTTC | SEQ ID NO. 278 |
| R36 | ATGGTCTCATCAGATGTGCCTCCTT | SEQ ID NO. 279 |
| R37 | CATGGTCTCATCAGATGTGCCTCCT | SEQ ID NO. 280 |
| R38 | CCATGGTCTCATCAGATGTGCCTCC | SEQ ID NO. 281 |
| R39 | GCCATGGTCTCATCAGATGTGCCTC | SEQ ID NO. 282 |
| R40 | AGCCATGGTCTCATCAGATGTGCCT | SEQ ID NO. 283 |
| R41 | GAGCCATGGTCTCATCAGATGTGCC | SEQ ID NO. 284 |
| R42 | GGAGCCATGGTCTCATCAGATGTGC | SEQ ID NO. 285 |
| R43 | GGGAGCCATGGTCTCATCAGATGTG | SEQ ID NO. 286 |
| R44 | AGGGAGCCATGGTCTCATCAGATGT | SEQ ID NO. 287 |
| R45 | CAGGGAGCCATGGTCTCATCAGATG | SEQ ID NO. 288 |
| R46 | CCAGGGAGCCATGGTCTCATCAGAT | SEQ ID NO. 289 |
| R47 | GCCAGGGAGCCATGGTCTCATCAGA | SEQ ID NO. 290 |
| R48 | GGCCAGGGAGCCATGGTCTCATCAG | SEQ ID NO. 291 |
| R49 | AGGCCAGGGAGCCATGGTCTCATCA | SEQ ID NO. 292 |
| R50 | CAGGCCAGGGAGCCATGGTCTCATC | SEQ ID NO. 293 |
| R51 | TCAGGCCAGGGAGCCATGGTCTCAT | SEQ ID NO. 294 |
| R52 | TTCAGGCCAGGGAGCCATGGTCTCA | SEQ ID NO. 295 |
| R53 | ATTCAGGCCAGGGAGCCATGGTCTC | SEQ ID NO. 296 |
| R54 | CAATTCAGGCCAGGGAGCCATGGTCT | SEQ ID NO. 297 |
| R55 | CCTCAGTGGGCTCATCTAT | SEQ ID NO. 298 |
| R56 | TCCCTTGGAAGAAACAGAGAAT | SEQ ID NO. 299 |
| R57 | CCCAATTCAGGCCAGGGA | SEQ ID NO. 300 |
| R58 | CAGGTGCCTCAGTGTTATCT | SEQ ID NO. 301 |
| R59 | TGGTCTTCAAAGCTTTCATTTAT | SEQ ID NO. 302 |
| R60 | GGGGTCATCCACCTCAGT | SEQ ID NO. 303 |
| R61 | CCCTTCGAGGTACTTATCGG | SEQ ID NO. 304 |
| R62 | GCTTTCATTTATGACTCCACTG | SEQ ID NO. 305 |
| R63 | TCTTGGTTACAGGTGCCTCA | SEQ ID NO. 306 |
| R64 | AAGAGTGGGTAGGTTCCAGG | SEQ ID NO. 307 |
| R65 | TGGGCTCATCTATCAGTGTA | SEQ ID NO. 308 |
| R66 | GGAGCCATGGTCTTCAAA | SEQ ID NO. 309 |
| R67 | CTGGGCATCTCCCAATTC | SEQ ID NO. 310 |
| R68 | ACAGAGAATCTTCCCTTTGGTG | SEQ ID NO. 311 |
| R69 | GAGTAGGACGGCAGAAGTT | SEQ ID NO. 312 |
| R70 | CAGTGTAGCCGTGGAGTAG | SEQ ID NO. 313 |
| R71 | GGAAGGCGCTACTAAGAATATC | SEQ ID NO. 314 |
| R72 | ACCTCAGTGGGCTCATCTAT | SEQ ID NO. 315 |
| R73 | CTTCCCTTTGGTGTCTCTCT | SEQ ID NO. 316 |
| R74 | TCCCAATCCCTTGGAAGAAAC | SEQ ID NO. 317 |
| R75 | TGTCTCTCTCTGACCACTTGA | SEQ ID NO. 318 |
| R76 | CCCCTTCGAGGTACTTATCGG | SEQ ID NO. 319 |
| R77 | ATCCCTTGGAAGAAACAGAGAAT | SEQ ID NO. 320 |
| R78 | AGGGGTCATCCACCTCAGT | SEQ ID NO. 321 |
| R79 | ATCTTGGTTACAGGTGCCTCA | SEQ ID NO. 322 |
| R80 | AAGAGTGGGTAGGTTCCAGGG | SEQ ID NO. 323 |
| R81 | GTGGGCTCATCTATCAGTGTA | SEQ ID NO. 324 |
| R82 | CTGGGCATCTCCCAATTCA | SEQ ID NO. 325 |
| R83 | ACAGGTGCCTCAGTGTTATCT | SEQ ID NO. 326 |
| R84 | GGAGTAGGACGGCAGAAGTT | SEQ ID NO. 327 |
| R85 | CCAATCCCTTGGAAGAAACA | SEQ ID NO. 328 |
| R86 | GTGTCTCTCTCTGACCACTTGA | SEQ ID NO. 329 |
| R87 | CCTCAGTGGGCTCATCTATCA | SEQ ID NO. 330 |
| R88 | GGCTCATCTATCAGTGTAGCC | SEQ ID NO. 331 |
| R89 | TTGGTTACAGGTGCCTCA | SEQ ID NO. 332 |
| R90 | AAGAGTGGGTAGGTTCCAGGGG | SEQ ID NO. 333 |
| R91 | GGCAGAAGTTCAATCTTGGTTAC | SEQ ID NO. 334 |
| R92 | CTGGGCATCTCCCAATTCAG | SEQ ID NO. 335 |
| R93 | TACAGGTGCCTCAGTGTTATCT | SEQ ID NO. 336 |
| R94 | AACAGAGAATCTTCCCTTTGGTG | SEQ ID NO. 337 |

TABLE 4-continued

Downstream Primers for Detecting Fusion Genotype of SLC34A2-ROS1

| | | |
|---|---|---|
| R95 | TGGAGTAGGACGGCAGAAGTT | SEQ ID NO. 338 |
| R96 | GAGTCCTGAAGAGTGGGTAG | SEQ ID NO. 339 |
| R97 | TCAGTGTAGCCGTGGAGTAG | SEQ ID NO. 340 |
| R98 | TGGAAGGCGCTACTAAGAATATC | SEQ ID NO. 341 |
| R99 | TGGAAGGCGCTACTAAGA | SEQ ID NO. 342 |
| R100 | AGGTGCCTCAGTGTTATCT | SEQ ID NO. 343 |
| R101 | CTCAGTGGGCTCATCTATCA | SEQ ID NO. 344 |
| R102 | GTCTCTCTCTGACCACTTGA | SEQ ID NO. 345 |
| R103 | AGTGTAGCCGTGGAGTAG | SEQ ID NO. 346 |
| R104 | AGTCCTGAAGAGTGGGTAG | SEQ ID NO. 347 |
| R105 | CCCTTGGAAGAAACAGAGAAT | SEQ ID NO. 348 |
| R106 | TTCCCTTTGGTGTCTCTCT | SEQ ID NO. 349 |
| R107 | AGTAGGACGGCAGAAGTT | SEQ ID NO. 350 |
| R108 | CCCAATCCCTTGGAAGAAAC | SEQ ID NO. 351 |
| R109 | AAGTAGAGAAATCCGAGAAGTAAA | SEQ ID NO. 352 |
| R110 | GCAGAAGTTCAATCTTGGTTAC | SEQ ID NO. 353 |
| R111 | TGGGCATCTCCCAATTCA | SEQ ID NO. 354 |
| R112 | CAGAGAATCTTCCCTTTGGTG | SEQ ID NO. 355 |
| R113 | GGCGCTACTAAGAATATCCAG | SEQ ID NO. 356 |
| R114 | AAATCAATCTCCCAATCCCTT | SEQ ID NO. 357 |
| R115 | AGAATATCCAGGGAGCACA | SEQ ID NO. 358 |
| R116 | AAGAGTGGGTAGGTTCCAG | SEQ ID NO. 359 |

TABLE 4-continued

Downstream Primers for Detecting Fusion Genotype of SLC34A2-ROS1

| | | |
|---|---|---|
| R117 | GCTCATCTATCAGTGTAGCC | SEQ ID NO. 360 |
| R118 | TGGTTACAGGTGCCTCA | SEQ ID NO. 361 |
| R119 | GGGTCATCCACCTCAGT | SEQ ID NO. 362 |
| R120 | CCCTTCGAGGTACTTATCG | SEQ ID NO. 363 |
| R121 | CCAATTCAGGCCAGGGA | SEQ ID NO. 364 |
| R122 | TTTGTTGGTCTCTTTGCTTT | SEQ ID NO. 365 |
| R123 | CATGGTCTTCAAAGCTTTCATTTATGACT | SEQ ID NO. 366 |
| R124 | CAGGGAGCCATGGTCTTCAA | SEQ ID NO. 367 |
| R125 | GAGCCATGGTCTTCAAAGCTTT | SEQ ID NO. 368 |
| R126 | GAGCCATGGTCTCATCAGATGTG | SEQ ID NO. 369 |
| R127 | GGAGCCATGGTCTCATCAG | SEQ ID NO. 370 |
| R128 | CAGGGAGCCATGGTCTCAT | SEQ ID NO. 371 |

The above-mentioned are merely for preferred examples of the present disclosure and not intended to limit the present disclosure. For one skilled in the art, various modifications and variations can be made to the present disclosure. Any amendments, equivalent replacements, improvements and so on made within the spirit and principle of the present disclosure should be covered within the scope of protection of the present disclosure.

INDUSTRIAL APPLICABILITY the circRNA with the base sequence as represented by any one of SEQ ID NOS. 1-6 disclosed in the present disclosure can be used as a biomarker for tumor detection or tumor auxiliary diagnosis, or used as a marker to detect whether the EML4-ALK fusion gene or the SLC34A2-ROS1 fusion gene occurs, and the purpose of rapid and convenient detection can be realized using this marker.

What is claimed is:

1. A method for treating a tumor in a subject, wherein the method comprises: obtaining a biological sample from the subject, determining that the biological sample has a circular RNA whose sequence is SEQ ID NO. 1 or 2, and then administering a therapeutically effective amount of an ALK inhibitor wherein the subject is a non-small cell lung cancer (NSCLC) patient with EML4-ALK fusion gene positive, the tumor is non-small cell lung cancer, and the ALK inhibitor is Crizotinib; or wherein the subject is a crizotinib-resistant ALK positive NSCLC patient with EML4-ALK fusion gene positive, the tumor is crizotinib-resistant ALK positive non-small cell lung cancer, and the ALK inhibitor is Ceritinib or Alectinib, and wherein the presence of the circular RNA whose sequence is SEQ ID NO: 1 or 2 is indicative of an EML4-ALK fusion gene positive NSCLC.

* * * * *